(12) United States Patent
Harada et al.

(10) Patent No.: US 7,718,703 B2
(45) Date of Patent: May 18, 2010

(54) NORVALINE DERIVATIVE AND METHOD FOR PREPARATION THEREOF

(75) Inventors: Naoyuki Harada, Osaka (JP); Masataka Hikota, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 48 days.

(21) Appl. No.: 11/795,966

(22) PCT Filed: Jan. 24, 2006

(86) PCT No.: PCT/JP2006/001394

§ 371 (c)(1),
(2), (4) Date: Jul. 25, 2007

(87) PCT Pub. No.: WO2006/080477

PCT Pub. Date: Aug. 3, 2006

(65) Prior Publication Data

US 2008/0076769 A1    Mar. 27, 2008

(51) Int. Cl.
A61K 31/16    (2006.01)
A61K 31/166    (2006.01)
C07C 229/06    (2006.01)

(52) U.S. Cl. .......................... 514/616; 560/37
(58) Field of Classification Search ............ 560/37
See application file for complete search history.

(56) References Cited

U.S. PATENT DOCUMENTS

2004/0242685 A1    12/2004    Morphy et al.

FOREIGN PATENT DOCUMENTS

| WO | WO-03/010132 A1 | 2/2003 |
| WO | WO 2005/021525 A1 | 3/2005 |
| WO | WO 2005/044810 A1 | 5/2005 |

OTHER PUBLICATIONS

Epilepsy [online] [retrieved Dec. 5, 2008] [retrieved from the internet, URL; http://www.nlm.nih.gov/medlineplus/ency/article/000694.htm.*
Wolin et al., "Novel glycine transporter type-2 reuptake inhibitors. Part 1: α-amino acid derivatives," Bioorganic & Medicinal Chemistry, vol. 12, No. 16, ISSN: 0968-0896, 2004, XP002382216, pp. 4477-4492.
Yoshida et al., "Preparation of N-(2-chloroisonicotinoyl) amino acid amides as agrochemical microbicides," XP002382218, 1989, pp. 773-781.
Caulfield, W.L. et al., "The First Potent and Selective Inhibitors of the Glycine Transporter Type 2", Journal of Medicinal Chemistry, vol. 44, No. 17, Jul. 25, 2001, pp. 2679-2682.
Isaac, M. et al., "5,5-Diaryl-2-amino-4-pentenoates as Novel, Potent, and Selective Glycine Transporter Type-2 Reuptake Inhibitors", Bioorganic & Medicinal Chemistry Letters, 11 (2001) pp. 1371-1373.
Ho, K. et al., "2-(Aminomethyl)-benzamide-based glycine transporter type-2 inhibitors", Bioorganic & Medicinal Chemistry Letters, 14 (2004), pp. 545-548.
Wolin R.L. et al., "Novel glycine transporter type-2 reuptake inhibitors. Part 2: β- and γ-amino acid derivatives", Bioorganic & Medicinal Chemistry, 12 (2004), pp. 4493-4509.
Wolin R. L. et al., "Inhibitors of the glycine transporter type-2 (GlyT-2): synthesis and biological activity of benzoylpiperidine derivatives", Bioorganic & Medicinal Chemistry, 12 (2004), pp. 4511-4532.

* cited by examiner

Primary Examiner—Rebecca L Anderson
Assistant Examiner—Shawquia Young
(74) Attorney, Agent, or Firm—Birch, Stewart, Kolasch & Birch, LLP.

(57) ABSTRACT

Norvaline derivative of the formula [I] or pharmaceutically acceptable salt thereof, method for preparing the same, pharmaceutical composition containing the same, and use of the compound for inhibiting transporting activity of glycine transporter type 2 (GlyT2)

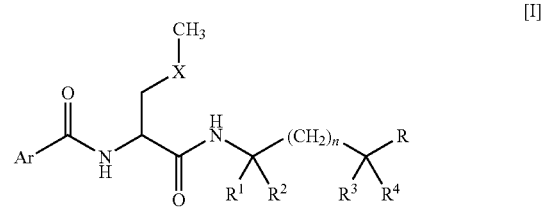

[I]

wherein X is —$CH_2$—, —O—, —S— or single bond; Ar is optionally substituted aryl or lower cycloalkyl; n is 0 to 2; $R^1$ and $R^2$ are (i) each is hydrogen or lower alkyl; (ii) $R^1$ and $R^2$ are combined to form lower alkylene; or (iii) $R^1$ is hydrogen or lower alkyl and $R^2$ is combined with $R^4$ or $R^6$ to form lower alkylene;

$R^3$ and $R^4$ are (i) each is hydrogen or lower alkyl; (ii) $R^3$ and $R^4$ are combined to form lower alkylene; or (iii) $R^3$ is hydrogen or lower alkyl and $R^4$ is combined with $R^2$ or $R^6$ to form lower alkylene;

R is

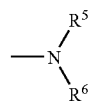

or —$OR^7$;

$R^5$ and $R^6$ are (i) each is optionally substituted lower alkyl, or hydrogen; (ii) $R^5$ and $R^6$ are combined to form aliphatic 5- to 6-membered heterocyclic group; or (iii) $R^5$ is optionally substituted lower alkyl or hydrogen and $R^6$ is combined with $R^2$ or $R^4$ to form lower alkylene; $R^7$ is lower alkyl.

13 Claims, No Drawings

NORVALINE DERIVATIVE AND METHOD FOR PREPARATION THEREOF

TECHNICAL FIELD

The present invention relates to a novel norvaline derivative, which exhibits an excellent inhibitory activity on glycine transporter type 2: GlyT2 and is useful as a medicament, and a method for preparation the same and a use thereof.

BACKGROUND ART

Glycine is one of inhibitory neurotransmitters. Glycine shows an inhibitory activity on sensory nerves through strychnine-sensitive glycine receptors (ssGlyRs) in the spinal cord and the brain stem of a vertebrate.

It has been reported that a pain threshold is elevated by intrathecal administration of glycine, while it is lowered by intrathecal administration of strychnine having a glycine receptor antagonistic activity. Those results suggest that a pain threshold may be kept at a certain level or higher by stimulation of strychnine-sensitive glycine receptors by glycine in the spinal cord.

On the other hand, for many neurotransmitters, there are reuptake systems into cells. Specific transporters are participated in those reuptake systems, whereby concentration of the neurotransmitter is controlled.

As glycine-specific transporters, there have been known two classes such as glycine transporter type 1: GlyT1 (including subtypes: GlyT1a, GlyT1b, GlyT1c) and glycine transporter type 2: GlyT2 (including subtypes: GlyT2a, GlyT2b), and genes thereof were cloned one after another in the 1990s [Guastella et al., Proc. Natl. Acad. Sci. USA, 1992, 89, 7189; Liu et al., FEBS Lett., 1992, 305, 110; Smith et al., Neuron, 1992, 8, 927; Borosky et al., Neuron, 1993, 10, 851].

Among these transporters for glycine, GlyT1 is widely distributed in the central nervous system: CNS, and existing mainly in glia cells and it has been considered that GlyT1 has a role to maintain a low concentration of glycine in an extracellular fluid.

On the contrary, GlyT2 exists locally in the brain stem and the spinal cord. GlyT2 takes a role in the reuptake system of glycine acting as a neurotransmitter in the brain stem and the spinal cord, and removes glycine from a synaptic space and inactivates glycinergic neuro-activity. Further, GlyT2 has the same distribution pattern as strychnine-sensitive glycine receptor: ssGlyR, and closely relates to the inhibitory system through strychnine-sensitive glycine receptors. Based upon this knowledge, it has been considered that the synaptic glycine level in the intrathecal space is elevated by inhibition of GlyT2 activity, and whereby the function of inhibitory neuron expressing ssGlyR is activated and then pain-related neurotransmission should be limited. Further, compounds which inhibit the transporting activity of GlyT2 (GlyT2 inhibitor) have been considered as being useful as a muscle relaxant, an anesthetic, an analgesic, etc. for treatment of muscle spasticity, tinnitus, epilepsy, neuropathic pain, etc. [Isaac et al., Bioorg. Med. Chem. Lett. 2001, 11, 1371-1373; WO2003/1013-2 (Akzo Nobel); Caulfield et al., J. Med. Chem., 2001, 44: 2679-2682; Ho et al., Bioorganic & Medicinal Chemistry Letters, 2004, 14, 545-548; Friauf et al., J. Comp. Neurol., 1999, 412, 17; Simpson et al., Neurochem. Res., 1996, 21, 1221; Huang et al., Neurol. Res., 2000, 22, 160; Gomeza et al., Curr. Opin. Drug Discovery Dev., 2003, 6, 675; Aragon., Eur. J. Pharmacol., 2003, 479, 249-262].

Further, it has actually been reported that a compound which inhibits the transporting activity of GlyT2 (GlyT2 inhibitor) shows an effect of improving hyperalgesia by increasing a pain threshold in neuropathic pain models [Houghton et al., 31$^{st}$ Society of Neuroscience Meeting Abstracts 2001, 27 (Abs 283.1)].

Further, GlyT2 inhibitors are considered as being useful for treatment of urological disorders [WO 2005/94808 (Bayer Healthcare)].

Consequently, GlyT2 inhibitors have been expected to be developed as an excellent medicament. Particularly, neuropathic pain syndromes are difficult to be cured, and available medicaments for neuropathic pain such as µ-Opioid, etc. often show side effects to the central nervous system, and thus, it has strongly been demanded to develop an excellent medicament therefor.

As to compounds which inhibit the transportation activity of GlyT2 (GlyT2 inhibitor), the following reports have been found.

For instance, amino acid derivatives having GlyT2 inhibiting activity are disclosed in the literature of Isaac et al. (Isaac et al, Bioorg. Med. Chem. Lett. 2001, 11, 1371-1373) (NPS); benzamide derivatives such as N-[(1-dimethylaminocycloalkyl)methyl]benzamide derivatives, 2-(aminomethyl) benzamide derivatives, etc. are disclosed in WO 2003/10132 (Akzo Nobel), the literature of Caulfield et al. (Caulfield et al., Journal of Medicinal Chemistry, 2001, 44, 2679-2682) and the literature of Ho et al. (Ho et al., Bioorganic & Medicinal Chemistry Letters, 2004, 14, 545-548).

Further, α, β and γ amino acid derivatives are disclosed in the literatures of Wolin et al. (Wolin et al., Bioorganic & Medicinal Chemistry, 2004, 12:4477-4492; Wolin et al., Bioorganic & Medicinal Chemistry, 2004, 12:4493-4509) and WO 2005/044810 (Janssen Pharmaceutica).

Still further, aryl piperidine amide derivatives are disclosed in the literatures of Wolin et al. (Wolin et al., Bioorganic & Medicinal Chemistry, 2004, 12:4511-4532) and WO 2005/021525 (Janssen Pharmaceutica).

DISCLOSURE OF INVENTION

The present invention provides a novel compound having an excellent inhibitory activity on glycine transporter type 2: GlyT2, a method for preparation thereof, and a use of the same and a pharmaceutical composition containing said compound etc.

The present inventors have intensively studied and have found a norvaline derivative having an excellent inhibitory activity on glycine transporter type 2: GlyT2 to accomplish the present invention.

Namely, the present invention relates to a norvaline derivative of the formula [I]:

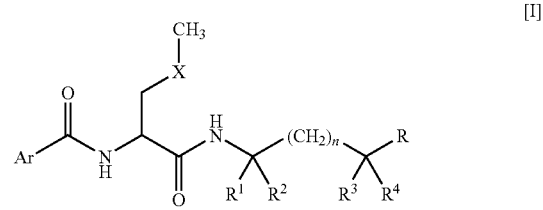

[wherein
X is —CH$_2$—, —O—, —S— or a single bond;
Ar is an optionally substituted aryl or an optionally substituted lower cycloalkyl;
n is an integer of 0 to 2;

$R^1$ and $R^2$ are the following (i), (ii) or (iii):
(i) each is independently a hydrogen atom or a lower alkyl;
(ii) $R^1$ and $R^2$ are combined together to form a lower alkylene; or
(iii) $R^1$ is a hydrogen atom or a lower alkyl and $R^2$ is combined together with $R^4$ or $R^6$ to form a lower alkylene, when R is

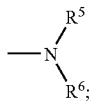

$R^3$ and $R^4$ are the following (i), (ii) or (iii):
(i) each is independently a hydrogen atom or a lower alkyl;
(ii) $R^3$ and $R^4$ are combined together to form a lower alkylene; or
(iii) $R^3$ is a hydrogen atom or a lower alkyl and $R^4$ is combined together with $R^2$ or $R^6$ to form a lower alkylene, when R is

R is

or —$OR^7$;
$R^5$ and $R^6$ are the following (i), (ii) or (iii):
(i) each is independently a lower alkyl optionally substituted with hydroxyl group(s), or a hydrogen atom;
(ii) $R^5$ and $R^6$ are combined together with the adjacent nitrogen atom to form an optionally substituted nitrogen-containing aliphatic 5 to 6-membered heterocyclic group;
(iii) $R^5$ is a lower alkyl optionally substituted with hydroxyl group(s), or a hydrogen atom, and $R^6$ is combined together with $R^2$ or $R^4$ to form a lower alkylene;
$R^7$ is a lower alkyl;
provided that when $R^5$ and $R^6$ are combined together with the adjacent nitrogen atom to form a morpholine ring, then Ar has at least one substituent other than halogen atom, methoxy or phenyl;
and when R is —$OR^7$ and X is a single bond, then Ar is an optionally substituted phenyl, an optionally substituted naphthyl or an optionally substituted lower cycloalkyl], or a pharmaceutically acceptable salt thereof.

Further, the present invention relates to a method for preparation of the above compound [I] or a pharmaceutically acceptable salt thereof.

Further, the present invention relates to a pharmaceutical composition containing the above compound [I] or a pharmaceutically acceptable salt thereof as an active ingredient.

Further, the present invention relates to a method for treatment or prophylaxis of a disease or condition, which comprises administering an effective amount of the above compound [I] or a pharmaceutically acceptable salt thereof to a patient.

Still further, the present invention relates to a use of the above compound [I] or a pharmaceutically acceptable salt thereof for manufacture of a medicament.

Still further, the present invention relates to a use of the above compound [I] or a pharmaceutically acceptable salt thereof for the inhibition of a transporting activity of glycine transporter type 2 (GlyT2).

The desired compound [I] of the present invention or a pharmaceutically acceptable salt thereof exhibits an excellent inhibitory activity on glycine transporter type 2: GlyT2. The pharmaceutical composition containing the desired compound of the present invention is useful as an active ingredient in a medicament for treatment or prophylaxis of a disease or condition (such as pain) which may be expected to be improved by inhibition of glycine transporter type 2: GlyT2.

BEST MODE FOR CARRYING OUT THE INVENTION

The desired compound [I] of the present invention may have optical isomers, and the present invention includes any of these isomers and also a mixture thereof.

In the present invention, the lower alkyl group, the lower alkylthio group, the lower alkylsulfonyl group, the lower alkoxy group, and the lower alkylamino group include a straight chain or branched chain groups having 1-6 carbon atoms ($C_{1-6}$), particularly ones having 1-4 carbon atoms ($C_{1-4}$).

The lower alkanoyl group and the lower alkanoylamino group include ones having 2-7 carbon atoms ($C_{2-7}$), particularly ones having 2-5 carbon atoms ($C_{2-5}$).

The lower alkanoyl group includes either one of a lower alkyl-CO— or a lower cycloalkyl-CO—.

The lower cycloalkyl group and the lower cycloalkenyl group include ones having 3-8 carbon atoms ($C_{3-8}$), particularly ones having 3-6 carbon atoms ($C_{3-6}$).

The lower alkylene group includes a straight chain or branched chain groups having 1-6 carbon atoms ($C_{1-6}$), particularly ones having 1-4 carbon atoms ($C_{1-4}$).

The lower alkenyl group and the lower alkenylene group include ones having 2-7 carbon atoms ($C_{2-7}$), particularly ones having 2-5 carbon atoms ($C_{2-5}$).

Further, the halogen atom includes, for example, a fluorine atom, a chlorine atom, a bromine atom or an iodine atom.

The optionally substituted amino group includes, for example, unsubstituted amino group and mono- or di-substituted non-cyclic amino group, and further includes cyclic amino group (e.g., 1-pyrrolidinyl, 1-piperidyl, 1-piperazinyl, morpholin-4-yl, etc.).

In the desired compound [I] of the present invention, the aryl moiety of the "optionally substituted aryl" represented by Ar includes a monocyclic or a bicyclic aryl, including monocyclic or bicyclic aromatic hydrocarbon group, and also including monocyclic or bicyclic aromatic heterocyclic group (heteroaryl). Said aryl specifically includes, for example, phenyl and naphthyl etc.

The lower cycloalkyl moiety of the "optionally substituted lower cycloalkyl" represented by Ar includes ones having 3-8 carbon atoms ($C_{3-8}$), more preferably ones having 3-6 carbon atoms ($C_{3-6}$). Said lower cycloalkyl specifically includes, for example, cyclohexyl etc.

The substituent(s) of the "optionally substituted aryl" or "optionally substituted lower cycloalkyl" represented by Ar may be one or more (preferably 1 to 3), and includes, for example, halogen atom (such as Cl, F, etc.); nitro group; cyano group; hydroxyl group; optionally substituted amino group [e.g., amino group optionally substituted with 1 or 2 substituent(s) selected from lower alkyl and formyl, etc.]; $C_{1-7}$ alkyl; optionally substituted $C_{1-12}$ alkoxy [e.g., lower alkoxy optionally substituted with phenyl which is optionally substituted with group(s) selected from halogen atom, lower alkyl and halo(lower)alkyl, etc.]; lower cycloalkoxy; lower alkylthio group; optionally substituted phenyl [e.g., phenyl optionally substituted with group(s) selected from halogen atom, lower alkyl and lower alkoxy, etc.]; optionally substituted piperidyl [e.g., 1-piperidyl optionally substituted with group(s) selected from lower alkyl and phenyl, etc.]; optionally substituted phenoxy [e.g., phenoxy optionally substituted with halogen atom(s), etc.]; and the like.

The lower alkyl represented by $R^1$, $R^2$, $R^3$ or $R^4$ may be methyl, etc.

The lower alkylene formed by combining $R^1$ and $R^2$ or $R^3$ and $R^4$ may be, for example, n-propane-1,3-diyl, n-butane-1,4-diyl, etc.

The lower alkylene formed by combining $R^2$ and $R^4$, $R^2$ and $R^6$, or $R^4$ and $R^6$ may be, for example, n-propane-1,3-diyl, n-butane-1,4-diyl, etc.

The lower alkyl moiety of the "optionally substituted lower alkyl" represented by $R^5$ or $R^6$ may be, for example, methyl, etc., and the substituent(s) thereof may be one or more (preferably 1 to 3) and includes, for example, hydroxyl, etc.

The nitrogen-containing aliphatic 5- to 6-membered heterocycle moiety of the "optionally substituted nitrogen-containing aliphatic 5- to 6-membered heterocyclic group" formed by combining $R^5$ and $R^6$ together with the adjacent nitrogen atom may be, for example, 1-pyrrolidinyl, 1-piperidyl, 1-piperazinyl, morpholin-4-yl, etc. Among them, 1-pyrrolidinyl, 1-piperidyl and 1-piperazinyl are preferable, and particularly 1-pyrrolidinyl is preferable.

The substituent(s) of the "optionally substituted nitrogen-containing aliphatic 5- to 6-membered heterocyclic group" (the substituent on the ring) may be one or more (preferably 1 to 3), and includes, for example, a lower alkyl group (e.g., methyl, etc.) or the like.

The lower alkyl represented by $R^7$ may be methyl, etc.

The preferred compounds of the compounds [I] of the present invention are the group of compounds having a chemical structure of the formula [Ia]:

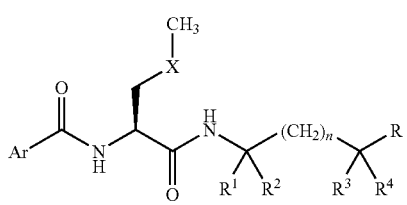

wherein the symbols are as defined above.

Besides, among the compounds [I] of the present invention or the above-mentioned groups of compounds, other preferred groups of compounds are ones wherein X is —CH₂—.

Further, among the compounds [I] of the present invention or the above-mentioned groups of compounds, other preferred groups of compounds are ones wherein X is —O—.

Further, among the compounds [I] of the present invention or the above-mentioned groups of compounds, other preferred groups of compounds are ones wherein X is —S—.

Further, among the compounds [I] of the present invention or the above-mentioned groups of compounds, other preferred groups of compounds are ones wherein X is a single bond.

Among the compounds [I] of the present invention or the above-mentioned group of compounds, further preferred group of compounds are ones wherein Ar is a group selected from a substituted phenyl and a substituted naphthyl.

Still further, among the compounds [I] of the present invention or the above-mentioned group of compounds, preferred group of compounds are those wherein R is

Specifically preferred compounds are the free form of the compounds described in Examples hereinafter or a pharmaceutically acceptable salt thereof.

The compounds [I] of the present invention may be either in the free form or in the form of a pharmaceutically acceptable salt.

The pharmaceutically acceptable salt includes, for example, a salt with an inorganic acid such as hydrochloride, sulfate, nitrate, phosphate and hydrobromide, and a salt with an organic acid such as acetate, fumarate, oxalate, citrate, methanesulfonate, benzenesulfonate, p-toluenesulfonate and maleate. When the compound of the present invention has a substituent such as a carboxyl group, the pharmaceutically acceptable salt thereof includes, for example, a salt with a base such as an alkali metal salt (e.g., sodium salt, potassium salt, etc.) and an alkaline earth metal salt (e.g., calcium salt, etc.).

The desired compounds [I] of the present invention and a salt thereof include any of intramolecular salts or adduct or their solvates or hydrates as well.

The desired compounds [I] of the present invention or a pharmaceutically acceptable salt thereof exhibit an excellent inhibitory activity on glycine transporter type 2: GlyT2, and said activity shows a high selectivity to GlyT2. Namely, the desired compounds [I] of the present invention or a pharmaceutically acceptable salt thereof show a higher inhibitory activity on glycine transporter type 2: GlyT2 in comparison with that on glycine transporter type 1: GlyT1 (more particularly GlyT1b, etc.).

Further, the desired compounds [I] of the present invention and a pharmaceutically acceptable salt thereof exhibit various pharmacological effects through their inhibitory activity on GlyT2. Thus, the desired compounds [I] of the present invention and a pharmaceutically acceptable salt thereof, and a pharmaceutical composition containing the same as an active ingredient may be used for inhibition of GlyT2, and these compounds or the pharmaceutical compositions containing the same may be used for treatment or prophylaxis of a disease or condition which can be expected to be improved by inhibition of GlyT2.

Compounds having an inhibitory activity on a transporting activity of GlyT2 (GlyT2 inhibitors) are considered to elevate a glycine level in the glycinergic nerve terminals in the spinal cord through the GlyT2 inhibitory activity thereof when administered into a living body of a vertebrate. Thus, GlyT2 inhibitors are considered to be useful through their GlyT2 inhibitory activity, for example, as a muscle relaxant, an anesthetic, an analgesic, etc. for treatment of muscle spasticity, tinnitus, epilepsy, pain, etc. [Isaac et al., Bioorg. Med. Chem. Lett. 2001, 11, 1371-1373; WO2003/10132 (Akzo Nobel); Caulfield et al., J. Med. Chem., 2001, 44:2679-2682; Ho et al., Bioorganic & Medicinal Chemistry Letters, 2004, 14, 545-548; Friauf et al., J. Comp. Neurol., 1999, 412, 17; Simpson et al., Neurochem. Res., 1996, 21, 1221; Huang et al., Neurol. Res., 2000, 22, 160; Gomeza et al., Curr. Opin. Drug Discovery Dev., 2003, 6, 675; Aragon., Eur. J. Pharmacol., 2003, 479, 249-262].

Further, GlyT2 inhibitors are considered to be useful through their GlyT2 inhibitory activity for treatment of urological disorders [WO 2005/94808 (Bayer Healthcare)].

Thus, the desired compounds [I] of the present invention or a pharmaceutically acceptable salt thereof, or a pharmaceutical composition containing the same as an active ingredient may be used for inhibition of a transporting activity of GlyT2, and also for activating glycinergic neuron in the spinal cord through its GlyT2 inhibitory activity by administration into a living body of a vertebrate. Further, the desired compounds [I] of the present invention or a pharmaceutically acceptable salt thereof, or a pharmaceutical composition containing the same as an active ingredient may preferably be used for treatment or prophylaxis of a disease or condition which can be expected to be improved by inhibition of GlyT2, namely for muscle spasticity, tinnitus, epilepsy, pain (particularly inflammatory pain and neuropathic pain, etc.) etc.

A method for administration of an effective amount of the desired compound [I] of the present invention or a pharmaceutically acceptable salt thereof to a patient are also useful for the above-mentioned objects of the present invention and are inclusive in the present invention.

Further, an use of the desired compound [I] of the present invention or a pharmaceutically acceptable salt thereof for manufacture of a medicament are also useful for the above-mentioned objects of the present invention and are inclusive in the present invention.

The inhibitory activity on GlyT2 and the pharmacological effects of the compounds of the present invention can be confirmed by the following known methods or a similar method thereto.

The inhibitory activity on glycine transporters (GlyT2 or GlyT1) can be detected by using cells expressing GlyT2 or GlyT1. The selectivity of the compound to GlyT2 can be determined by comparing the inhibitory activity on GlyT2 with that on GlyT1.

The detection of the inhibitory activity on glycine uptake by cells expressing GlyT2 or GlyT1 can be carried out by a method disclosed in the literatures (Caulfield et al., J. Med. Chem., 2001, 44, 2679-2682; Williams et al., Anal. Biochem., 2003, 321, 31-37; Morrow et al., FEBS Letters, 1998, 439, 334-340; etc.).

The effect on inflammatory pain can be detected in the following experimental systems using the mouse or rat.
Formalin test:
  (Bannon et al., J. Pharmacol. Exp. Ther., 1998, 285, 787-794)
Inflammatory pain model:
  (Taniguchi et al., Br. J. Pharmacol., 1997, 122, 809-812; Clayton et al., Pain, 2002, 96, 253-260; Walker et al., J. Pharmacol. Exp. Ther., 2003, 304, 56-62)
Model of hyperalgesia after thermal injury:
  (Nozaki-Taguchi et al., Neurosci. Lett., 1998, 254, 25-28)
Model of incisional pain:
  (Brennan et al., Pain, 1996, 64, 493-501)

The effect on neuropathic pain can be detected in the following experimental systems using the mouse or rat.

Chronic constriction injury model:
  (Bennett et al., Pain, 1988, 33, 87-107)
Segmental spinal nerve ligation model:
  (Kim et al., Pain, 1992, 50, 355-363)
Partial sciatic nerve ligation model:
  (Seltzers et al., Pain, 1990, 43, 205-218)
Diabetic neuropathy model:
  (Bannon et al., Brain Res., 1998, 801, 158-163)

In case of using the compound [I] of the present invention or a pharmaceutically acceptable salt thereof as an active ingredient for medical purpose, it is used together with an inert carrier suitable for each administration route. For this purpose, it can be formulated into a conventional pharmaceutical preparation (tablets, granules, capsules, powders, solutions, suspensions, emulsions, injections, drops, etc.), and used. The carrier includes, for example, any conventional pharmaceutically acceptable ones, such as binders (gum Alabicum, gelatin, sorbitol, polyvinylpyrrolidone, etc.), excipients (lactose, sucrose, corn starch, sorbitol, etc.), lubricants (magnesium stearate, talc, poly-ethylene glycol, etc.), disintegrators (potato starch, etc.). In case of injections and drops, it can be formulated with using distilled water for injection, physiological saline, an aqueous glucose solution, etc.

The administration route of the compound [I] of the present invention or a pharmaceutically acceptable salt thereof for medical use is not limited, and usual oral or parenteral routes (intravenous, intramuscular, subcutaneous, transdermal, transnasal, transmucosal, intestinal, etc.) can be applied.

The dosage of the compound [I] of the present invention or a pharmaceutically acceptable salt thereof for medical use can adequately be set forth within a range of an effective amount being capable of exhibiting the desired pharmacological effect in accordance with the potency and characteristics of the active compound. The dosage may vary depending on the administration routes, the age, the body weight and the conditions of the patient, and it is set forth adequately within a usual dosage range such as 0.001-300 mg/kg per day.

The desired compound of the present invention [I] may be prepared by the following Method A or Method B, though it is not limited thereto.

[Method A]

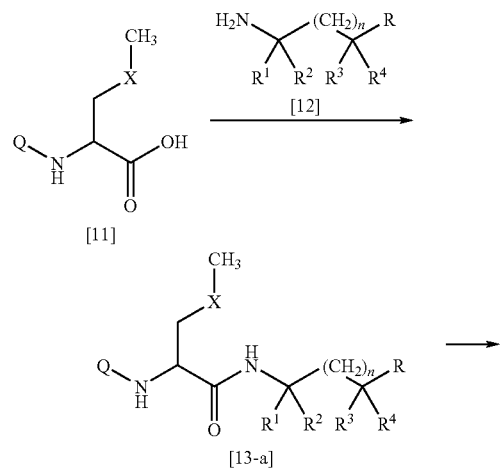

-continued

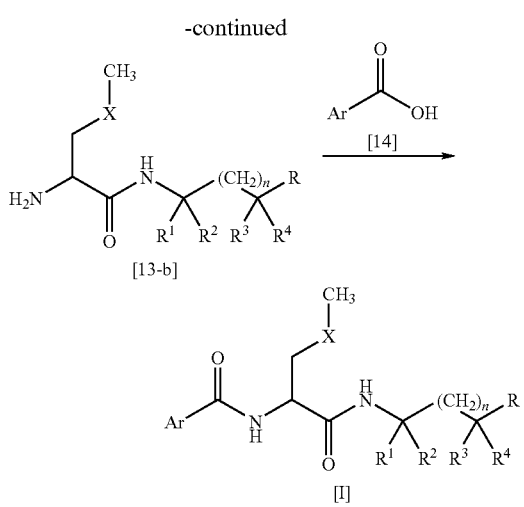

The desired compound [I] of the present invention can be prepared, for example, as follows:

At first, a compound of the formula [11] (wherein Q is a protecting group for an amino group, and the other symbols are as defined above) or a salt thereof is reacted with a compound of the formula [12] (wherein the symbols are as defined above) or a salt thereof to give a compound of the formula [13-a] (wherein the symbols are as defined above) or a salt thereof.

The protecting group for the amino group is removed from the compound [13-a] or a salt thereof to give a compound of the formula [13-b] (wherein the symbols are as defined above) or a salt thereof.

The compound [13-b] or a salt thereof is reacted with a compound of the formula [14] (wherein the symbols are as defined above) or a salt thereof, followed by converting the resultant into a pharmaceutically acceptable salt thereof, if necessary, to give the desired compound of the formula [I].

As the protecting group for an amino group of Q, any conventional protecting groups for an amino group such as t-butoxy-carbonyl group, benzyloxycarbonyl group, trifluoroacetyl group, 9-fluorenylmethyloxycarbonyl group, etc. can be suitably used.

As the salts of the compounds [11], [12], [13-a], [13-b] and [14], for example, a salt with an inorganic acid such as hydrochloride and sulfate, an alkali metal salt such as sodium salt and potassium salt, an alkaline earth metal salt such as magnesium salt and calcium salt, etc. can be used.

The reaction of the above Method A is carried out as follows.

The reaction of the compound [11] or a salt thereof and the compound [12] or a salt thereof may be carried out in a suitable solvent in the presence of a condensing agent, and further, if necessary, in the presence or absence of an additive and/or a base.

As the condensing agent, EDC (1-(3-dimethylaminopropyl)-3-ethylcarbodiimide) or a hydrochloride thereof, DCC (dicyclohexyl-carbodiimide), 1,3-diisopropylcarbodiimide, DEPC (diethylphosphoryl cyanide), O-(7-azabenzotriazol-1-yl)-N,N,N',N'-tetramethyluronium hexafluorophosphate, O-benzotriazol-1-yl-N,N,N',N'-tetramethyl-uronium hexafluorophosphate, chloroformic acid esters (e.g. ethyl chloroformate, isobutyl chloroformate, etc.), 2,4,6-trichlorobenzoyl chloride, carbonyldiimidazole, etc. can be suitably used.

Further, in order to accelerate the reaction or to prevent a side reaction (e.g. racemization), an additive such as 1-hydroxybenzotriazole, 1-hydroxy-7-azabenzotriazole, 3,4-dihydro-3-hydroxy-4-oxo-1,2,3-benzotriazine, 1-hydroxysuccinimide, dimethylaminopyridine, etc. can be added together with the above condensing agent.

As the base, an organic base (e.g. triethylamine, diisopropyl-ethylamine, N-methylmorpholine, pyridine, dimethylaniline, dimethyl-aminopyridine, etc.), an alkali metal carbonate (e.g. sodium carbonate, potassium carbonate, etc.), an alkali metal (e.g. sodium hydroxide, potassium hydroxide, etc.), etc. can be suitably used.

The reaction preferably proceeds at −20° C. to 100° C., more preferably at 0° C. to 40° C.

The solvent may be any one which does not show an adverse affect upon the reaction, and for example, acetonitrile, N,N-dimethyl-formamide, tetrahydrofuran, diethyl ether, dioxane, ethyl acetate, toluene, methylene chloride, dichloroethane, chloroform, N,N-dimethyl-acetamide, 1,3-dimethyl-2-imidazolidinone, 1-methyl-2-pyrrolidinone, 1,2-dimethoxyethane, xylene, or a mixture of two or more thereof can be suitably used.

Removal of the protecting group for an amino group (Q) from the compound [13-a] or a salt thereof may be carried out in a conventional manner, for example, by an acid treatment using trifluoroacetic acid etc., by a base treatment or by a catalytic reduction, in a suitable solvent or without a solvent.

The reaction of the compound [13-b] or a salt thereof and the compound [14] or a salt thereof may be carried out in the same manner as in the reaction of the compound [11] or a salt thereof and the compound [12] or a salt thereof.

[Method B]

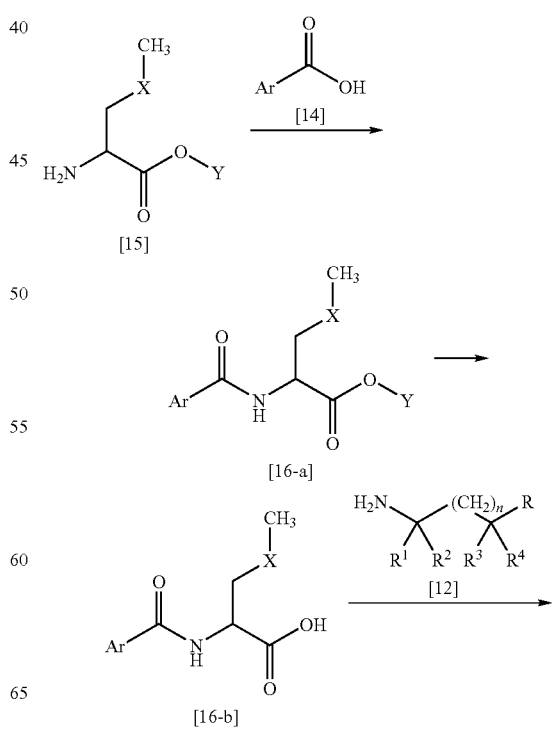

-continued

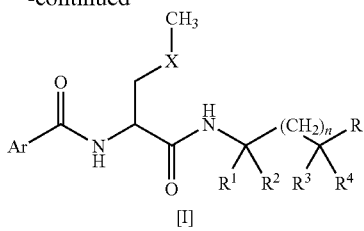

[I]

The desired compound of the present invention [I] can also be prepared by the following method.

At first, a compound of the formula [15] (wherein Y represent a protecting group for a carboxyl group, and the other symbols are as defined above) or a salt thereof is reacted with the compound [14] or a salt thereof to give a compound of the formula [16-a] (wherein the symbols are as defined above) or a salt thereof.

By removing the protecting group for a carboxyl group from the compound [16-a] or a salt thereof, a compound of the formula [16-b] (wherein the symbols are as defined above) or a salt thereof is obtained.

The compound [16-b] or a salt thereof is reacted with the above compound [12] or a salt thereof, followed by converting the resultant into a pharmaceutically acceptable salt thereof, if necessary, to give the desired compound of the formula [I].

As the protecting group for a carboxyl group of Y, any conventional protecting groups for a carboxyl group such as methyl group, benzyl group, allyl group, t-butyl group, etc. can be suitably used.

As the salts of the compound [12] and [14], the same ones as mentioned above may be used, and as the salts of the compound [15], [16-a] and [16-b], a salt with an inorganic acid such as hydrochloride and sulfate, or an alkali metal salt such as sodium salt and potassium salt can be used.

The reaction of the above Method B is carried out as follows.

The reaction of the compound [15] or a salt thereof and the compound [14] or a salt thereof may be carried out in the same manner as in the reaction of the compound [11] or a salt thereof and the compound [12] or a salt thereof.

The removal of the protecting group for a carboxyl group (Y) from the compound [16-a] or a salt thereof may be carried out in a conventional manner, for example, by alkali-hydrolysis in a suitable solvent, by hydrogenolysis using a palladium catalyst in a suitable solvent or without a solvent, or by an acid treatment using trifluoro-acetic acid or hydrogen chloride etc.

The reaction of the compound [16-b] or a salt thereof and the compound [12] or a salt thereof can be carried out in the same manner as in the reaction of the compound [11] or a salt thereof and the compound [12] or a salt thereof.

The starting compounds in the above Method A and Method B can be prepared by a known method and/or in the same manner as one described in Reference Examples as described hereinafter.

Further, the desired compound [I] prepared by the above Methods (Method A or Method B) can be structurally converted into other desired compound [I] by a method disclosed in Examples as described hereinafter, a conventional method and/or a combination thereof.

The compound [I] of the present invention prepared as above or a starting compound therefor may be isolated and purified either in the free form or in the form of a salt thereof. The salt may be prepared by a conventional method for preparation of a salt. Isolation and purification can be carried out by a conventional chemical procedure such as extraction, concentration, crystallization, filtration, recrystallization, various kinds of chromatography, etc.

In the compound of the present invention, optical isomers such as racemic isomers, optically active isomers, diastereomers, etc. can be present alone or as mixture thereof. A stereochemically pure isomer can be obtained by using a stereochemically pure starting compound or by separating an optical isomer according to the general separation process for racemic resolution. A mixture of diastereomers may be separated by a conventional method, for example, by fractional crystallization or chromatography, etc.

The present invention is illustrated in more details by Examples, but it should not be construed to be limited thereto.

In Table A, Table B, Table C, Table D, Table E and Table of Reference Examples as described hereinafter, the chemical structures and the physical properties, etc. of the compounds of Examples and Reference Examples are shown.

In Tables, MS.APCI (m/z), MS.ESI (m/z) and MS.EI (m/z) indicate mass spectrometric data.

(APCI: atmospheric pressure chemical ionization mass spectrum, ESI: electrospray ionization mass spectrum, EI: electron ionization mass spectrum).

Additionally, in the specification, the meanings of abbreviations are as follows:

[Me]: a methyl group,
[Et]: an ethyl group,
[Bu]: a butyl group,
[Boc]: a tert-butoxycarbonyl group,
[Ts]: a p-toluenesulfonyl group.

Experiment 1 Glycine uptake assay (GlyT2 and GlyT1 assay)

Inhibitory activity on GlyT2 and GlyT1 was examined by glycine uptake assays using cells expressing GlyT2 or GlyT1, as described in the literatures, Caulfield et al. (J. Med. Chem., 2001, 44, 2679-2682), Williams et al. (Anal. Biochem., 2003, 321, 31-37, etc.), and/or Morrow et al. (FEBS Letters, 1998, 439: 334-340).

Briefly, the assays were performed as follows.

HEK 293 cells stably transfected with either human GlyT2 or human GlyT1b were used. The cells were grown in 96-well Cytostar-T™ scintillating microplates (20,000-40,000 cells/well) overnight before removal of culture medium and addition of HEPES buffered saline containing glycine (10 μM) labeled with $^{14}C$ and varying concentrations of test compounds.

Plates were incubated at room temperature for 2-3 hours, and then, the plates were counted in a plate counter.

Data were analyzed by the sigmoid dose-response curve fitting to produce $IC_{50}$ (the concentration of test compound producing 50% inhibition) values.

As a result of the assay, it was shown that the compound of Example 1.026 has specific inhibitory activity on GlyT2, where $IC_{50}$ value in GlyT2 assay was lower than 10 nM, while $IC_{50}$ value in GlyT1 assay was more than 100 times higher than that in GlyT2 assay.

EXAMPLES

Example 1.001

(1) To a solution of tert-butoxycarbonyl-L-norvaline (1.50 g), 1-(3-dimethylaminopropyl)-3-ethylcarbodiimide hydrochloride (1.99 g) and 1-hydroxybenzotriazole (933 mg) in chloroform (20 ml) were added N,N-dimethylethylenediamine (0.758 ml) and triethylamine (0.962 ml) in this order, and the mixture was stirred at room temperature for 16 hours. To the reaction mixture was added water (30 ml), and the reaction mixture was stirred vigorously for 10 minutes, and the organic layer was separated. The aqueous layer was further extracted with chloroform. The organic layers were combined and washed with 1% aqueous potassium carbonate solution and saturated saline, and dried over anhydrous sodium sulfate, followed by removing the solvent under reduced pressure. The residue was purified by silica gel column chromatography [solvent: methanol-chloroform (1:10)] to obtain $N^2$-(tert-butoxycarbonyl)-N'-[2-(dimethylamino) ethyl]-L-norvalinamide (1.67 g).

MS-APCI(m/z): 288 [M+H]$^+$ (2) To a solution of the compound (1.67 g) obtained in the above (1) in dioxane (5 ml) was added 4N solution of hydrogen chloride in dioxane (5 ml), and the mixture was stirred at room temperature for 2 hours. To the reaction mixture was added diethyl ether, and the mixture was stirred at room temperature for further 30 minutes. The precipitated powder was collected by filtration and dried under reduced pressure to obtain $N^1$-[2-(dimethylamino)ethyl]-L-norvalinamide dihydrochloride (1.5 g).

MS-APCI(m/z): 188 [M+H]$^+$ (3) To a solution of the compound (1.0 g) obtained in the above (2), 4-hexyloxybenzoic acid (854 mg) and 1-hydroxybenzotriazole (513 mg) in N,N-dimethylformamide (20 ml) were added 1-(3-dimethyl-aminopropyl)-3-ethylcarbodiimide hydrochloride (1.09 g) and triethyl-amine (2.1 ml) in this order, and the mixture was stirred at room temperature for 15 hours. To the reaction mixture was added water (100 ml), and the mixture was stirred vigorously for 10 minutes, and extracted with ethyl acetate. The organic layer was washed with water, 1% aqueous potassium carbonate solution and saturated saline, and dried over anhydrous sodium sulfate, and the solvent was evaporated under reduced pressure. The residue was purified by silica gel column chromatography [solvent: ammonium hydroxide-methanol-chloroform (1:2: 20)] and recrystallized from isopropyl ether to obtain N-[(1S)-1-[[[2-(dimethylamino)ethyl]amino]carbonyl]butyl]-4-(hexyloxy)benzamide (845 mg, the compound of Example 1.001 listed in Table as described hereinafter).

Examples 1.002-1.035

In the same manner as in the above Example 1.001, the compounds of Examples 1.002-1.035 listed in Table as described hereinafter were obtained.

Example 1.036

(1) In the same manner as in Example 1.001, N-[(1S)-1-[[[1-(dimethylamino)cyclopentyl]methyl]amino]carbonyl]butyl]-4-(hexyloxy)-3-(nitro) benzamide was obtained.

(2) To a solution of the compound (207 mg) obtained in the above (1) in methanol (12 ml) was added 10% palladium on activated carbon (100 mg). The mixture was subjected to catalytic hydrogenation under atmospheric pressure. After 5 hours, the catalyst was removed by filtration, and the filtrate was concentrated under reduced pressure. The residue was purified by silica gel column chromatography [NH] [solvent: methanol-chloroform (1:10)] to obtain 3-amino-N-[(1S)-1-[[[1-(dimethylamino)cyclopentyl] methyl]amino]carbonyl]butyl-4-(hexyloxy)-benzamide (187 mg, the compound of Example 1.036 listed in Table as described hereinafter).

Examples 1.037-1.081

In the same manner as in the above Example 1.001, the compounds of Examples 1.037-1.081 listed in Table as described hereinafter were obtained.

Example 1.082

To a solution of N-[(1S)-1-[[[1-(dimethylamino)cyclopentyl]-methyl]aminocarbonyl]butyl]-4-hexyloxy-3-(methoxymethoxy)benzamide (17 mg) (obtained in the same manner as in the above Example 1.001) in dioxane (3 ml) was added 4N solution of hydrogen chloride in dioxane (3 ml), and the mixture was stirred for 2 hours. The reaction mixture was concentrated under reduced pressure, and the residue was washed with diethyl ether to obtain N-[(1S)-1-[[[1-(dimethylamino)cyclopentyl]-methyl]aminocarbonyl] butyl]-4-hexyloxy-3-hydroxybenzamide hydrochloride (15 mg, the compound of Example 1.082 listed in Table as described hereinafter).

Example 2.001

In the same manner as in the above Example 1.001 using N-[(1,1-dimethylethoxy)carbonyl]-O-methyl-L-serine instead of tert-butoxycarbonyl-L-norvaline as a starting compound, the compound of Example 2.001 listed in Table as described hereinafter was obtained.

Examples 2.002-2.010

In the same manner as in the above Example 2.001, the compounds of Examples 2.002-2.010 listed in Table as described hereinafter were obtained.

Example 2.011

(1) N-[(1,1-Dimethylethoxy)carbonyl]-O-methyl-L-serine (439 mg) and 4-amino-1-benzylpiperidine (381 mg) were treated in the same manner as in the above Example 1.001 (1) to obtain [(1S)-1-(methoxy-methyl)-2-oxo-2-[[1-(phenylmethyl)-4-piperidyl]amino]ethyl]-carbamic acid 1,1-dimethylethyl ester.

MS-APCI(m/z): 392[M+H]$^+$ (2) To a solution of the compound (815 mg) obtained in the above (1) in methanol (15 ml), was added 20% palladium hydroxide on activated carbon (250 mg). The mixture was stirred vigorously for 2 hours under hydrogen atmosphere. The catalyst was removed from the reaction mixture by filtration, and the filtrate was concentrated under reduced pressure. The residue was dissolved in dichloromethane (10 ml) and cooled in an ice bath. While stirring vigorously, thereto were added dropwise 4N aqueous sodium hydroxide solution (1 ml) and a solution of 2,2,2-trichloroethyl chloroformate (508 mg) in dichloromethane (1 ml) simultaneously.

After stirring further for 30 minutes, the organic layer was collected. After extracting the aqueous layer with chloroform, organic layers were combined and washed with water and saturated saline. The organic layer was dried over anhydrous sodium sulfate, and the solvent was evaporated under reduced pressure. The residue was purified by silica gel column chromatography [solvent: hexane-ethyl acetate (2:3)] to obtain 4-[(2S)-2-(tert-butoxycarbonylamino)-3-(methoxy)propionylamino]piperidine-1-carboxylic acid 2,2,2-trichloroethyl ester (840 mg).
MS-APCI(m/z): 476/478[M+H]$^+$ (3) The compound (839 mg) obtained in the above (2) was treated in the same manner as in the above Example 1.001 (2) to obtain 4-[(2S)-2-amino-3-(methoxy)propionylamino]piperidine-1-carboxylic acid 2,2,2-trichloroethyl ester hydrochloride (594 mg).
MS-APCI(m/z): 376/378[M+H]$^+$ (4) The compound (250 mg) obtained in the above (3) and 4-benzyl-oxy-3,5-dimethoxybenzoic acid (174 mg) were treated in the same manner as in the above Example 1.001 (3) to obtain 4-[(2S)-2-(4-benzyl-oxy-3,5-dimethoxybenzoylamino)-3-methoxypropionylamino]piperidine-1-carboxylic acid 2,2,2-trichloroethyl ester (367 mg).
MS-APCI(m/z): 646/648[M+H]$^+$ (5) To a solution of the compound (365 mg) obtained in the above (4) in tetrahydrofuran (15 ml) were added acetate buffer (3 ml) and zinc powder (1.5 g), and the mixture was stirred at room temperature for 4.5 hours. Precipitates were removed by filtration, and the filtrate was concentrated under reduced pressure. To the resulted residue were added chloroform and saturated aqueous sodium bicarbonate solution, and the organic layer was collected. The organic layer was washed with saturated saline, and dried over anhydrous sodium sulfate. The solvent was evaporated under reduced pressure. The residue was purified by NH-silica gel column chromatography [solvent: chloroform-methanol (1:0 to 20:1)] to obtain 3,5-dimethoxy-N-[(1S)-1-(methoxy-methyl)-2-oxo-2-(4-piperidylamino)ethyl]-4-(phenylmethoxy)benzamide (246 mg, the compound of Reference Example 2.011 listed in Table as described hereinafter).

Example 3.001

(1) To a solution of L-norvaline methyl ester hydrochloride (1.68 g), 4-hexyloxybenzoic acid (2.22 g) and 1-hydroxybenzotriazole (1.35 g) in chloroform (30 ml) were added 1-(3-dimethylaminopropyl)-3-ethyl-carbodiimide hydrochloride (2.87 g) and triethylamine (2.8 ml) in this order, and the mixture was stirred at room temperature for 5 hours. To the reaction mixture was added water (30 ml), and the mixture was vigorously stirred for 10 minutes. The organic layer was collected, and the aqueous layer was further extracted with chloroform. The organic layer were combined, washed with 1% hydrochloric acid, water, 2% aqueous potassium carbonate solution and saturated saline, and dried over anhydrous sodium sulfate. The solvent was evaporated under reduced pressure, and the residue was purified by silica gel column chromatography [solvent: ethyl acetate-hexane (1:5)] to obtain N-[4-(hexyloxy)benzoyl]-L-norvaline methyl ester (3.21 g).
MS-APCI(m/z): 336 [M+H]$^+$ (2) A solution of the compound (3.20 g) obtained in the above (1) in methanol (20 ml) was cooled in an ice bath, and thereto was added 4N aqueous sodium hydroxide solution (6 ml). The mixture was stirred at room temperature for 1.5 hour. The reaction mixture was concentrated under reduced pressure, and the residue was dissolved in water. The mixture was cooled in an ice bath, and thereto was added dropwise a 10% hydrochloric acid while it was vigorously stirred. The mixture was extracted with chloroform, and the organic layer was washed with water and saturated saline, and dried over anhydrous sodium sulfate. The solvent was evaporated under reduced pressure, and the residue was purified by silica gel column chromatography [solvent: methanol-chloroform (1:10)] to obtain N-[4-(hexyloxy)benzoyl]L-norvaline (3.1 g).
MS-ESI(m/z): 320 [M−H]

(3) To a solution of the compound (64 mg) obtained in the above (2), 2-(1-methylpyrrolidin-2-yl)ethylamine (0.030 ml) and 1-hydroxybenzo-triazole (27 mg) in chloroform (3 ml) were added 1-(3-dimethylamino-propyl)-3-ethylcarbodiimide hydrochloride (58 mg) and triethylamine (0.028 ml) in this order, and the mixture was stirred at room temperature for 15 hours. To the reaction mixture was added water (3 ml), and the mixture was vigorously stirred for 10 minutes and extracted with ethyl acetate. The organic layer was washed with water, 1% aqueous potassium carbonate solution and saturated saline, and dried over anhydrous sodium sulfate. The solvent was evaporated under reduced pressure, and the residue was purified by silica gel column chromatography [NH] [solvent: methanol-chloroform (1:30)] to obtain 4-(hexyloxy)-N-[(1S)-1-[[[2-(1-methyl-2-pyrrolidinyl)ethyl]amino]-carbonyl]butyl]benzamide (68 mg, the compound of Example 3.001 listed in Table as described hereinafter).

Examples 3.002-3.003

The compounds of Examples 3.002-3.003 listed in Table as described hereinafter were obtained in the same manner as in the above Example 3.001.

Example 4.001-4.003

In the same manner as in the above Example 1.001 using (2S)-2-(tert-butoxycarbonylamino)-3-methylthiopropionic acid instead of tert-butoxycarbonyl-L-norvaline as a starting compound, the compounds of Example 4.001-4.003 listed in Table as described hereinafter were obtained.

Example 5.001-5.005

In the same manner as in the above Example 1.001 using (2S)-2-(tert-butoxycarbonylamino)-n-butanoic acid instead of tert-butoxy-carbonyl-L-norvaline as a starting compound, the compounds of Example 5.001-5.005 listed in Table as described hereinafter were obtained.

Reference Example 1.01

(1) To a solution of ethyl vanillate (589 mg) in acetone (15 ml) were added potassium carbonate (828 mg) and 1-bromo-hexane (0.632 ml) in this order. The mixture was heated under reflux for 24 hours. After the reaction mixture was cooled to room temperature, the precipitates were removed by filtration, and the filtrate was concentrated under reduced pressure. The residue was purified by silica gel column chromatography [solvent: ethyl acetate-hexane (1:5)] to obtain 4-hexyloxy-3-methoxybenzoic acid ethyl ester (840 mg).
MS-APCI(m/z): 281 [M+H]$^+$ (2) A solution of the compound (836 mg) obtained in the above (1) in ethanol (15 ml) was cooled in an ice bath, and thereto was added a 4N aqueous sodium hydroxide solution (3 ml). The mixture was stirred at room temperature for 15 hours. The reaction mixture was concentrated under reduced pressure, and the residue was dissolved in water. The mixture was cooled in an ice bath, and thereto was added dropwise a 10% hydrochloric acid while the mixture was vigorously stirred. The mixture was extracted with chloroform, and the organic layer was washed with water and saturated saline, and dried over anhydrous sodium sulfate. The solvent was evaporated under reduced pressure, and the residue was purified by silica gel column chromatography [solvent: methanol-chloroform (1:15)] to obtain 4-hexyloxy-3-methoxybenzoic acid (666 mg, the compound of Reference Example 1.01 listed in Table as described hereinafter).

Reference Examples 1.02-1.07

The compounds of Reference Examples 1.02-1.07 listed in Table as described hereinafter were obtained in the same manner as in the above Reference Example 1.01.

Reference Example 1.08

(1) To a solution of 4-hydroxy-3,5-dimethylbenzoic acid (1.66 g) in N,N-dimethylacetamide (20 ml) were added potassium carbonate (5.52 g) and 1-bromohexane (4.2 ml) in this order, and the mixture was vigorously stirred at 100° C. for 20 hours. The reaction solution was cooled to room temperature and poured into water, and the mixture was extracted with ethyl acetate. The organic layer was washed with water and saturated saline, and dried over anhydrous sodium sulfate. The solvent was evaporated under reduced pressure, and the residue was purified by silica gel column chromatography [solvent: ethyl acetate-hexane (1:5)] to obtain 4-hexyloxy-3,5-dimethylbenzoic acid hexyl ester (3.34 g).
MS-APCI (m/z): 335 [M+H]$^+$
(2) To the compound (3.34 g) obtained in the above (1) in methanol (40 ml) was added 4N aqueous sodium hydroxide solution (10 ml). The mixture was stirred at 50° C. for 24 hours. The reaction solution was cooled to room temperature, and the reaction mixture was concentrated under reduced pressure. The residue was dissolved in water, and the mixture was cooled in an ice bath, and thereto was added dropwise 10% hydrochloric acid while the mixture was vigorously stirred. The mixture was extracted with chloroform, and the organic layer was washed with water and saturated saline, dried over anhydrous sodium sulfate, and the solvent was evaporated under reduced pressure. The residue was purified by silica gel column chromatography [solvent:methanol-chloroform (1:10)] to obtain 4-hexyloxy-3,5-dimethylbenzoic acid (2.50 g, the compound of Reference Example 1.08 listed in Table as described hereinafter).

Reference Examples 1.09-1.10

The compounds of Reference Examples 1.09-1.10 listed in Table as described hereinafter were obtained by the same manner as in the above Reference Example 1.08.

Reference Example 1.11

(1) A solution of 4-phenyl-1-butanol (1.50 g) and pyridine (3.2 ml) in methylene chloride (20 ml) was cooled in an ice bath, and thereto was added dropwise a solution of tosyl chloride (2.86 g) in methylene chloride (10 ml). The mixture was stirred for 2 hours, and washed with water, 10% hydrochloric acid and saturated saline, and dried over anhydrous magnesium sulfate. The solvent was evaporated under reduced pressure, and the residue was purified by silica gel column chromatography [solvent: ethyl acetate-hexane (1:5)] to obtain 4-phenyl-butyl 4-methylbenzene-sulfonate (1.60 g).
MS-EI (m/z): 304 [M]$^+$
(2) Using the compound obtained in the above (1) and methyl 4-hydroxybenzoate, 4-(4-phenylbutoxy)benzoic acid (the compound of Reference Example 1.11 listed in Table as described hereinafter) was obtained in the same manner as in the above Reference Example 1.01.

Reference Example 1.12-1.23

In the same manner as in the above Reference Example 1.01, the compounds of Examples 1.12-1.23 listed in Table as described hereinafter were obtained.

Reference Example 1.24-1.27

In the same manner as in the above Reference Example 1.08, the compounds of Examples 1.24-1.27 listed in Table as described hereinafter were obtained.

Reference Example 1.28

(1) To a solution of 4-fluorobenzoic acid methyl ester (500 μl) in dimethylacetamide (5 ml) were added n-hexylamine (635 μl) and potassium carbonate (0.8 g) in this order. The mixture was stirred at 80° C. for 20 hours. The reaction mixture was cooled to room temperature, and thereto was added water. The reaction mixture was extracted with ethyl acetate.

The organic layer was washed with saturated saline, and dried over anhydrous sodium sulfate. The solvent was evaporated under reduced pressure, and the residue was purified by silica gel column chromatography [solvent: hexane-ethyl acetate (99:1 to 9:1)] to obtain 4-(hexylamino)benzoic acid methyl ester (439 mg).
MS-APCI(m/z): 236[M+H]$^+$
(2) To a solution of the compound (400 mg) obtained in the above (1) in methanol (12 ml) were added a 4N aqueous sodium hydroxide solution (2.1 ml), and the mixture was stirred for 24 hours at 50° C. The reaction mixture was cooled to room temperature, and methanol was evaporated under reduced pressure. To an aqueous solution of the residue, while cooling in an ice bath, was added 6N hydrochloride (1.4 ml) to neutralize. Then the mixture was extracted with ethyl acetate.

The organic layer was washed with saturated saline, and dried over anhydrous sodium sulfate. The solvent was evaporated under reduced pressure, and the residue was purified by silica gel column chromatography [solvent: hexane-ethyl acetate (9:1 to 3:1)] to obtain 4-(hexylamino)benzoic acid (312 mg, the compound of Reference Example 1.28 listed in Table as described hereinafter).

Reference Example 1.29-1.30

In the same manner as in the above Reference Example 1.28, the compounds of Examples 1.29-1.30 listed in Table as described hereinafter were obtained.

Reference Example 1.31

(1) Ethyl 3,4-dihydroxybenzoate was treated in the same manner as in the above Reference Example 1.01 (1) to obtain ethyl 4-hexyloxy-3-hydroxybenzoate.
(2) A solution of the compound (100 mg) obtained in the above (1) in chloroform (5 ml) was cooled in an ice bath, and thereto were added chloromethyl methyl ether (43 μl) and diisopropylethylamine (96 μl) in this order. The mixture was stirred at room temperature for 3 days. The reaction mixture was washed with water, saturated aqueous sodium bicarbonate solution and saturated saline, and thereafter, dried over anhydrous sodium sulfate. The solvent was evaporated under reduced pressure, and the residue was purified by silica gel column chromatography [solvent: hexane-ethyl acetate (99:1 to 92:8)] to obtain 4-hexyloxy-3-(methoxymethoxy)benzoic acid ethyl ester (115 mg).

MS-APCI(m/z): 328[M+NH$_4$]$^+$ (3) The compound (100 mg) obtained in the above (2) was treated in the same manner as in the above Reference Example 1.01 (2) to obtain 4-hexyloxy-3-(methoxymethoxy)benzoic acid (the compound of Reference Example 1.31 listed in Table as described hereinafter).

Reference Example 1.32

(1) To a solution of vanillic acid ethyl ester (500 mg) in trifluoroacetic acid (5 ml) was added hexamethylenetetramine (179 mg). The mixture was heated under reflux for 19 hours. The reaction mixture was cooled to room temperature, and concentrated under reduced pressure.

The residue was dissolved in ethyl acetate, washed with water and saturated saline, dried over anhydrous sodium sulfate. The solvent was evaporated under reduced pressure. The residue was purified by silica gel column chromatography [solvent: hexane-ethyl acetate(9:1 to 4:1)] to obtain 3-formyl-4-hydroxy-5-methoxybenzoic acid ethyl ester (177 mg).

MS-ESI(m/z): 223[M–H]$^-$ (2) To a solution of the compound (150 mg) obtained in the above (1) in methanol (15 ml) were added hydrochloric acid (one drop) and 10% palladium on activated carbon (75 mg). The mixture was stirred vigorously for 1 hour under hydrogen atmosphere. After removing the catalyst from the reaction mixture by filtration, the filtrate was concentrated under reduced pressure. The residue was purified by silica gel column chromatography [solvent: hexane-ethyl acetate (99:1 to 95:5)] to obtain 4-hydroxy-3-methoxy-5-methylbenzoic acid ethyl ester (129 mg).

MS-APCI(m/z): 211[M+H]$^+$ (3) The compound (100 mg) obtained in the above (2) was treated in the same manner as in the above Reference Example 1.01 to obtain 4-hexyloxy-3-methoxy-5-methylbenzoic acid (the compound of Reference Example 1.32 listed in Table as described hereinafter).

Reference Example 1.33

In the same manner as in the above Reference Example 1.31, the compound of Example 1.33 listed in Table as described hereinafter was obtained.

Reference Example 1.34

(1) 4-Hydroxy-3-nitrobenzoic acid methyl ester was treated in the same manner as in the above Reference Example 1.01 (1) to obtain 4-hexyloxy-3-nitrobenzoic acid methyl ester.

(2) To a solution of the compound (615 mg) obtained in the above (1) in methanol (15 ml) was added 10% palladium on activated carbon (150 mg). The mixture was stirred vigorously for 2 hours under hydrogen atmosphere. After removing the catalyst from the reaction mixture by filtration, the filtrate was concentrated under reduced pressure. The residue was purified by silica gel column chromatography [solvent: hexane-ethyl acetate(5:1)] to obtain 3-amino-4-hexyloxybenzoic acid ethyl ester (445 mg).

MS-APCI(m/z): 252[M+H]$^+$ (3) To a solution of the compound (100 mg) obtained in the above (2) in chloroform (3 ml) were added 1-(3-dimethylaminopropyl)-3-ethyl-carbodiimide hydrochloride (159 mg) and formic acid (30 µl). The mixture was stirred at room temperature for 3.5 hours. The reaction mixture was washed with water and saturated saline, and dried over anhydrous sodium sulfate, followed by removing the solvent under reduced pressure. The residue was purified by silica gel column chromatography [solvent: hexane-ethyl acetate (9:1 to 4:1)] to obtain 3-(formylamino)-4-hexyloxybenzoic acid methyl ester (104 mg).

MS-APCI(m/z): 297[M+NH$_4$]$^+$ (4) The compound obtained in the above (3) was treated in the same manner as in the above Reference Example 1.01 (2) to obtain 3-(formyl-amino)-4-hexyloxybenzoic acid (the compound of Reference Example 1.34 listed in Table as described hereinafter).

Reference Example 1.35

(1) A mixture of 6-bromo-2-naphthalenecarboxylic acid methyl ester (3.0 g), phenylboronic acid (2.07 g), dichlorobis(triphenylphosphine) palladium (II) (793 mg), 2M aqueous sodium carbonate solution (12 ml) and dimethoxyethane (48 ml) was stirred at 80° C. under argon atmosphere for 3.5 hours. The reaction solution was cooled to room temperature, and thereto was added ethyl acetate, and the mixture was stirred vigorously for about 10 hours. The resulting precipitate was removed by filtration. The filtrate was diluted with ethyl acetate, and washed with water and saturated saline. The organic layer was dried over anhydrous sodium sulfate, and the solvent was evaporated under reduced pressure. The residue was purified by silica gel column chromatography [solvent: chloroform-hexane (2:1)] to obtain 6-phenyl-2-naphthalenecarboxylic acid methyl ester.

MS-APCI(m/z): 263[M+H]$^+$ (2) To a suspension of the compound (410 mg) obtained in the above (1) in methanol-tetrahydrofuran (1:1, 20 ml) was added 4N aqueous sodium hydroxide solution (1.56 ml), and the mixture was stirred at 80° C. for 12 hours. The reaction solution was cooled to room temperature, and diluted with water, and washed with diethyl ether. To the obtained aqueous phase was added dropwise 10% hydrochloric acid, and the mixture was extracted with ethyl acetate. The extract was washed with saturated saline, dried over anhydrous sodium sulfate, and the solvent was evaporated under reduced pressure. The resulting powdery residue was washed with isopropyl ether, and dried under reduced pressure to obtain 6-phenyl-2-naphthalenecarboxylic acid (158 mg, the compound of Reference Example 1.35 listed in Table as disclosed hereinafter).

Reference Example 1.36-1.38

In the same manner as in the above Reference Example 1.35, the compounds of Examples 1.36-1.38 listed in Table as described hereinafter were obtained.

Reference Example 1.39

(1) A suspension of 6-hydroxy-2-naphthalenecarboxylic acid methyl ester (7.0 g) in acetic acid (100 ml) was cooled in an ice bath, and thereto was added dropwise a concentrated nitric acid (52.5 ml). The mixture was stirred for 30 minutes while cooling in an ice bath. The reaction mixture was poured into ice water, and then extracted with ethyl acetate.

The organic layer was washed with water and saturated saline, and dried over anhydrous sodium sulfate. The solvent was evaporated under reduced pressure, and the residue was purified by silica gel column chromatography [solvent: hexane-ethyl acetate (3:1)] to obtain 6-hydroxy-5-nitro-2-naphthalenecarboxylic acid methyl ester (5.1 g)

MS-ESI (m/z): 246 [M–H]$^-$ (2) A solution of the compound (2.93 g) obtained in the above (1) in chloroform (100 ml) was cooled in an ice bath, and thereto were added pyridine (3.83 ml) and anhydrous trifluoromethanesulfonic acid (3.99 ml) in this order. The mixture was stirred at room temperature for 19 hours. The reaction mixture was washed with water, 5% hydrochloric acid and saturated saline, and was dried over anhydrous sodium sulfate.

The solvent was evaporated under reduced pressure. To the residue were added chloroform and hexane, and the mixture was stirred. The precipitate was collected by filtration to obtain 5-nitro-6-(trifluoro-methanesulfonyloxy)-2-naphthalenecarboxylic acid methyl ester (3.51 g).

MS-APCI(m/z): 397[M+NH$_4$]$^+$ (3) To a solution of the compound (260 mg) obtained in the above (2) in dimethoxyethane (6 ml) were added phenylboric acid (125 mg) tetrakis(triphenylphosphine)palladium (80 mg) and 2M aqueous sodium carbonate solution in this order. The mixture was stirred at 80° C. for 3 hours. The reaction mixture was cooled to room temperature, and thereto were added ethyl acetate and water, and the mixture was stirred for 1 hour. The organic layer was collected, washed with water and saturated saline, and dried over anhydrous sodium sulfate. The solvent was evaporated under reduced pressure. The residue was purified by silica gel column chromatography [solvent: hexane-ethyl acetate (4:1)] to obtain 5-nitro-6-phenyl-2-naphthalenecarboxylic acid methyl ester (175 mg).

MS-APCI(m/z): 308[M+H]$^+$ (4) The compound obtained in the above (3) was treated in the same manner as in the above Reference Example 1.01 (2) to obtain 5-nitro-6-phenyl-2-naphthalenecarboxylic acid (the compound of Reference Example 1.39 listed in Table as described hereinafter).

Reference Example 1.40

(1) To a solution of 5-nitro-6-(trifluoromethanesulfonyloxy)-2-naphthalenecarboxylic acid (100 mg) in acetonitrile (5 ml) was added piperidine (80 μl). The mixture was heated under reflux for 2.5 hours. The reaction mixture was cooled to room temperature, and then concentrated under reduced pressure. The residue was purified by silica gel column chromatography [solvent: hexane-ethyl acetate (9:1)] to obtain 5-nitro-6-piperidino-2-naphthalenecarboxylic acid methyl ester (83 mg).

MS-APCI (m/z): 315 [M+H]$^+$ (2) The compound (80 mg) obtained in the above (1) was dissolved in methanol-tetrahydrofuran (1:1) (6 ml), and thereto was added 4N aqueous sodium hydroxide solution (0.32 ml). The mixture was stirred at room temperature for 19 hours. The reaction mixture was concentrated under reduced pressure. The residue was dissolved in water, and thereto was added dropwise 6N hydrochloric acid while cooling in an ice bath. After stirring at room temperature for 1 hour, the precipitate was collected by filtration and dried under reduced pressure to obtain 5-nitro-6-piperidino-2-naphthalenecarboxylic acid (58 mg, the compound of Reference Example 1.40 listed in Table as described hereinafter).

Reference Example 1.41

(1) To a solution of 6-hydroxy-2-naphthalenecarboxylic acid methyl ester (202 mg) in chloroform (10 ml) were added copper(II) acetate (218 mg), Molecular sieves 4A (200 mg), 4-fluorophenylboronic acid (280 mg) and triethylamine (0.697 ml) in this order. The mixture was stirred at room temperature for 22 hours. To the reaction mixture was added a saturated aqueous sodium bicarbonate solution, and the mixture was stirred at room temperature for 30 minutes. The organic layer was collected. The aqueous layer was further extracted with chloroform. The organic layers were combined, washed with saturated saline, and dried over anhydrous sodium sulfate. The solvent was evaporated under reduced pressure. The residue was purified by silica gel column chromatography [solvent: hexane-ethyl acetate (9:1)] to obtain 6-(4-fluorophenyloxy)-2-naphthalenecarboxylic acid methyl ester (119 mg).

MS-APCI(m/z): 297[M+H]$^+$ (2) The compound obtained in the above (1) was treated in the same manner as in the above Reference Example 1.40 (2) to obtain 6-(4-fluorophenyloxy)-2-naphthalenecarboxylic acid (the compound of Reference Example 1.41 listed in Table as described hereinafter). Reference Example 2.01

(1) The mixture of dimethylamine hydrochloride (8.16 g) and acetone (5.81 g) was cooled in an ice bath, and thereto was added dropwise a solution of potassium cyanide (6.52 g) in water (50 ml). The mixture was stirred at room temperature for 22 hours. The reaction mixture was extracted with ethyl acetate. The organic layer was washed with saturated saline, and dried over anhydrous sodium sulfate. The solvent was evaporated under reduced pressure to obtain 2-(dimethylamino)-2-methylpropionitrile.

(2) A suspension of lithium aluminum hydride (10.36 g) in tetrahydrofuran (150 ml) was cooled in an ice bath under argon atmosphere, and thereto was added dropwise a solution of sulfuric acid (13.4 g) in tetrahydrofuran (30 ml). After the mixture was stirred for 1 hour, thereto was added dropwise a solution of the compound obtained in the above (1) in tetrahydrofuran (30 ml). The reaction mixture was taken of from the ice bath and stirred for 1.5 hours. Then, the reaction mixture was cooled again in an ice bath, and thereto were added dropwise water (10.4 ml) and 4N aqueous sodium hydroxide solution (31.2 ml) in this order.

The reaction mixture was taken off from ice bath and stirred for 12 hours. Precipitates were removed by filtration, and the filtrate was concentrated under reduced pressure. The residue was dissolved in dioxane (10 ml), and thereto was added 4N solution of hydrogen chloride in dioxane, and the mixture was stirred at room temperature for 30 minutes. The reaction mixture was concentrated under reduced pressure. To the residue was added ethanol (100 ml), and the mixture was stirred at room temperature for 30 minutes. The precipitate was collected by filtration and dried under reduced pressure to obtain 2-dimethylamino-2-methylpropylamine (9.7 g, the compound of Reference Example 2.01 listed in Table as described hereinafter).

Reference Example 2.02-2.04

In the same manner as in the above Reference Example 2.01, the compounds of Examples 2.02-2.04 listed in Table as described hereinafter were obtained.

Reference Example 2.05

(1) A suspension of sodium hydride (2.96 g) in diethyl ether was cooled in an ice bath, and thereto was added dropwise a solution of diethyl cyanomethylphosphonate (13.4 g) in diethyl ether (30 ml). Then, thereto was added dropwise a solution of cyclopentanone (5.65 g) in diethyl ether (10 ml), and the mixture was stirred for 10 minutes while cooling. The reaction mixture was warmed to room temperature, and then stirred for 12 hours. To the reaction mixture was added water, and after stirred for a while, the mixture was extracted with diethyl ether. The organic layer was washed with saturated saline, and dried over anhydrous sodium sulfate. The solvent was evaporated under reduced pressure to obtain cyclopentylideneacetonitrile.

(2) To the compound obtained in the above (1) (1 g) was added 30% methylamine-methanol solution (11 ml). The mixture was heated in a bath of temperature 60° C. and stirred for 19 hours in a sealed tube.

The reaction mixture was cooled to room temperature, and concentrated under reduced pressure. To the residue were added ethyl acetate and 5% hydrochloride, and aqueous layer was collected. The aqueous layer was cooled in an ice bath, and thereto was added potassium carbonate. The aqueous layer was concentrated under reduced pressure, and to the residue was added methanol. Precipitates were removed by filtration. The filtrate was concentrated under reduced pressure, and the residue was purified by silica gel column chromatography [NH] [solvent: chloroform] to obtain (1-(methylamino)cyclopentyl)acetonitrile (479 mg).

MS-APCI(m/z): 139[M+H]$^+$ (3) To a solution of the compound (479 mg) obtained in the above (2) in dichloromethane (20 ml) were added 37% aqueous formalin solution (0.5 ml), sodium cyanoborohydride (240 mg) and acetic acid (0.6 ml) in this order. The mixture was stirred at room temperature for 4 hours. To the reaction mixture was added aqueous solution of potassium carbonate, and after stirred for a while, the mixture was extracted with 10% methanol-chloroform. The organic layer was washed with saturated saline, and dried over anhydrous sodium sulfate. The solvent was evaporated under reduced pressure. The residue was purified by silica gel column chromatography [solvent: chloroform-methanol (10:1)] to obtain (1-(dimethylamino) cyclopentyl)acetonitrile (458 mg).

MS-APCI(m/z): 153 [M+H]$^+$ (4) The compound obtained in the above (3) was treated in the same manner as in the above Reference Example 2.01 (1) to obtain [1-(2-aminoethyl)cyclopentyl]dimethylamine dihydrochloride (the compound of Reference Example 2.05 listed in Table as described hereinafter).

TABLE A

| Ex. No. | Ar | $R^1$ $R^2$ $R^3$ $R^4$ $(CH_2)_n$ R | Salt | Physical properties, etc. |
|---|---|---|---|---|
| 1.001 | H$_3$C-(CH$_2$)$_n$-O-C$_6$H$_4$- | -CH$_2$CH$_2$CH$_2$-N(CH$_3$)$_2$ | Free form | Melting point: 103-104° C. MS·APCI(m/z): 392 [M + H]+ |
| 1.002 | H$_3$C-(CH$_2$)$_n$-O-C$_6$H$_4$- | -CH$_2$CH$_2$CH$_2$-N(CH$_3$)$_2$ | Free form | MS·ESI(m/z): 378 [M + H]+ |
| 1.003 | H$_3$C-(CH$_2$)$_n$-O-C$_6$H$_3$(OCH$_3$)- | -CH$_2$CH$_2$CH$_2$-N(CH$_3$)$_2$ | Free form | MS·APCI(m/z): 422 [M + H]+ |
| 1.004 | H$_3$C-(CH$_2$)$_n$-O-C$_6$H$_2$(OCH$_3$)$_2$- | -CH$_2$CH$_2$CH$_2$-N(CH$_3$)$_2$ | Free form | MS·APCI(m/z): 452 [M + H]+ |

TABLE A-continued
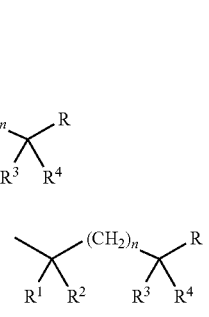
| Ex. No. | Ar | (CH₂)ₙ R<br>R¹ R² R³ R⁴ | Salt | Physical properties, etc. |
|---|---|---|---|---|
| 1.005 | 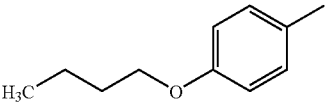 | 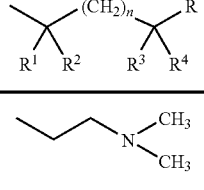 | Free form | MS · ESI(m/z): 364 [M + H]+ |
| 1.006 | 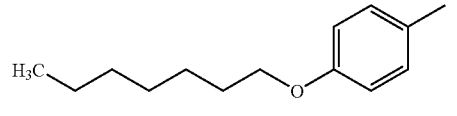 | 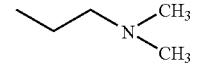 | Free form | MS · ESI(m/z): 406 [M + H]+ |
| 1.007 | 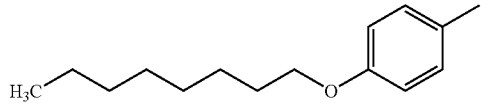 | 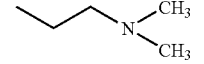 | Free form | MS · ESI(m/z): 420 [M + H]+ |
| 1.008 | 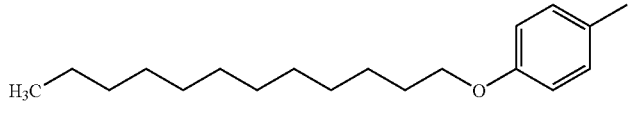 | 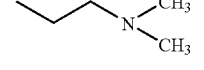 | Free form | MS · ESI(m/z): 476 [M + H]+ |
| 1.009 | 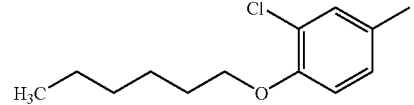 | 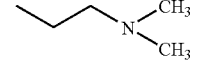 | Free form | MS · APCI(m/z): 426/428 [M + H]+ |
| 1.010 | 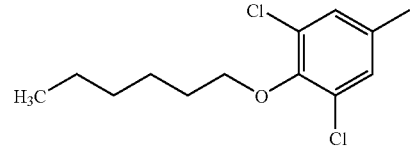 | 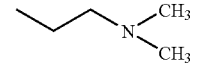 | Free form | MS · APCI(m/z): 460/462 [M + H]+ |
| 1.011 | 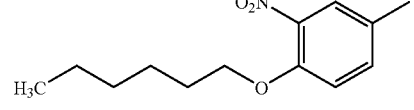 | 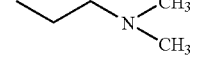 | Free form | MS · APCI(m/z): 437 [M + H]+ |
| 1.012 | 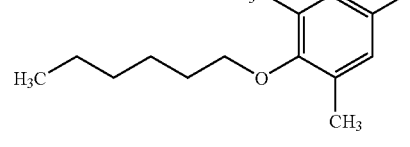 | 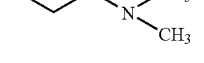 | Free form | Melting point: 115.5-118.5° C. MS · APCI (m/z): 420 [M + H]+ |
| 1.013 | 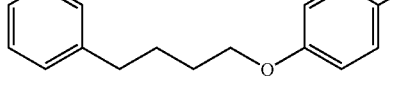 | 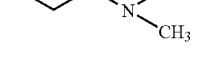 | Free form | MS · ESI(m/z): 440 [M + H]+ |

TABLE A-continued

| Ex. No. | Ar | (CH₂)ₙ R<br>R¹ R² R³ R⁴ | Salt | Physical properties, etc. |
|---|---|---|---|---|
| 1.014 | 2,6-dimethoxy-4-methyl-3-(benzyloxy)phenyl (H₃CO, OCH₃, OBn substituted) | propyl-N(CH₃)₂ | Free form | MS · APCI (m/z): 458 [M + H]+ |
| 1.015 | 4-pentylphenyl (H₃C-(CH₂)₄-C₆H₄-) | propyl-N(CH₃)₂ | Free form | MS · ESI(m/z): 376 [M + H]+ |
| 1.016 | 4-hexylphenyl (H₃C-(CH₂)₅-C₆H₄-) | propyl-N(CH₃)₂ | Free form | MS · ESI(m/z): 390 [M + H]+ |
| 1.017 | 4-biphenyl | propyl-N(CH₃)₂ | Free form | MS · ESI(m/z): 368 [M + H]+ |
| 1.018 | 4'-ethoxy-4-biphenyl (H₃CO-C₆H₄-C₆H₄-) | propyl-N(CH₃)₂ | Free form | MS · ESI(m/z): 412 [M + H]+ |
| 1.019 | 4'-propyl-4-biphenyl (H₃C-CH₂-CH₂-C₆H₄-C₆H₄-) | propyl-N(CH₃)₂ | Free form | MS · ESI(m/z): 410 [M + H]+ |
| 1.020 | 4-(pentyloxy)phenyl (H₃C-(CH₂)₄-O-C₆H₄-) | 1-ethyl-1-(dimethylaminomethyl)cyclopentyl | Free form | MS · APCI(m/z): 446 [M + H]+ |

TABLE A-continued

| Ex. No. | Ar | (CH₂)ₙ with R¹ R² R³ R⁴ | Salt | Physical properties, etc. |
|---|---|---|---|---|
| 1.021 | 4-methyl-2-methoxy-5-hexyloxyphenyl | 1-ethyl-1-(N,N-dimethylamino)cyclopentyl | Free form | MS·APCI(m/z): 476 [M + H]+ |
| 1.022 | 3,5-dimethoxy-4-butoxyphenyl | 1-ethyl-1-(N,N-dimethylamino)cyclopentyl | Free form | MS·APCI (m/z): 478 [M + H]+ |
| 1.023 | 3,5-dimethyl-4-hexyloxyphenyl | 1-ethyl-1-(N,N-dimethylamino)cyclopentyl | Free form | MS·APCI (m/z): 474 [M + H]+ |
| 1.024 | 2-cyano-4-methyl-(hexyloxy)phenyl | 1-ethyl-1-(N,N-dimethylamino)cyclopentyl | Free form | MS·APCI(m/z): 471 [M + H]+ |
| 1.025 | 3,5-dimethoxy-4-(phenethyloxy)phenyl | 1-ethyl-1-(N,N-dimethylamino)cyclopentyl | Free form | MS·APCI (m/z): 526 [M + H]+ |
| 1.026 | 3,5-dimethoxy-4-benzyloxyphenyl | 1-ethyl-1-(N,N-dimethylamino)cyclopentyl | Free form | MS·APCI (m/z): 512 [M + H]+ |

TABLE A-continued
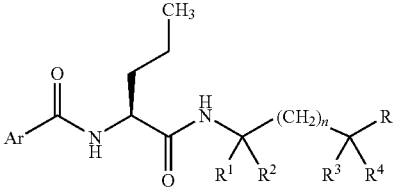
| Ex. No. | Ar | R1 R2 (CH2)n R3 R4 R | Salt | Physical properties, etc. |
|---|---|---|---|---|
| 1.027 | 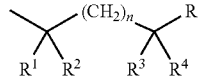 | 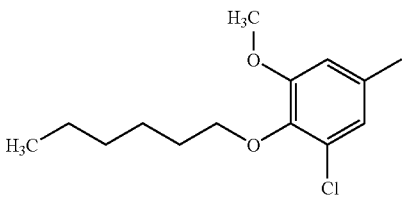 | Free form | MS · APCI(m/z): 510/512 [M + H]+ |
| 1.028 | 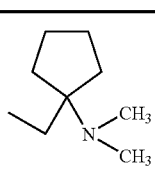 | 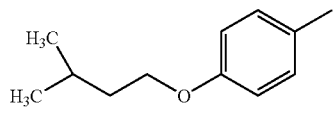 | Free form | MS · APCI (m/z): 432 [M + H]+ |
| 1.029 | 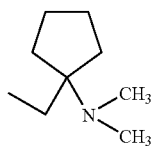 | 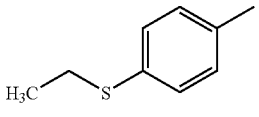 | Free form | MS · APCI (m/z): 406 [M + H]+ |
| 1.030 | 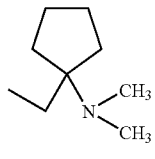 | 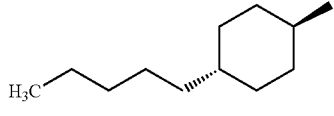 | Free form | MS · APCI (m/z): 422 [M + H]+ |
| 1.031 | 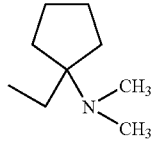 | 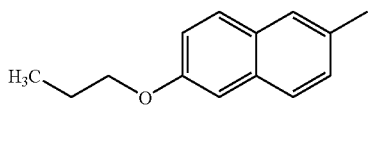 | Free form | MS · APCI(m/z): 454 [M + H]+ |
| 1.032 | 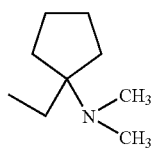 | 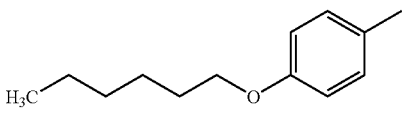 | Free form | MS · APCI(m/z): 432 [M + H]+ |
| 1.033 | 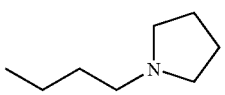 | 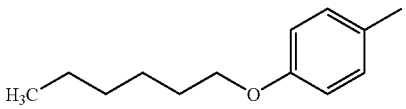 | Free form | MS · ESI(m/z): 446 [M + H]+ |
| 1.034 | 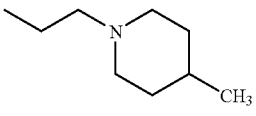 | 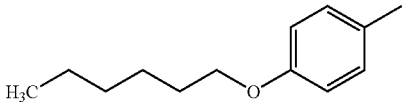 | Free form | MS · ESI(m/z): 447 [M + H]+ |

TABLE A-continued

| Ex. No. | Ar | R¹ R² (CH₂)ₙ R³ R⁴ R | Salt | Physical properties, etc. |
|---|---|---|---|---|
| 1.035 | H₃C–(CH₂)₅–O–C₆H₄– | –CH₂CH₂–O–CH₃ | Free form | MS·ESI(m/z): 379 [M + H]+ |
| 1.036 | H₃C–(CH₂)₅–O–C₆H₃(NH₂)– | 1-ethyl-1-(N,N-dimethylamino)cyclopentyl | Free form | MS·APCI (m/z): 461 [M + H]+ |
| 1.037 | 4-Cl-C₆H₄-CH₂-O-(3,5-dimethoxy)C₆H₂– | 1-ethyl-1-(N,N-dimethylamino)cyclopentyl | Free form | MS·APCI (m/z): 546/548 [M + H]+ |
| 1.038 | H₃C–(CH₂)₅–C₆H₄– | 1-ethyl-1-(N,N-dimethylamino)cyclopentyl | Free form | MS·APCI (m/z): 430 [M + H]+ |
| 1.039 | H₃C–(CH₂)₃–CH(CH₃)–O–C₆H₄– | 1-ethyl-1-(N,N-dimethylamino)cyclopentyl | Free form | MS·APCI (m/z): 446 [M + H]+ |
| 1.040 | H₃C–(CH₂)₅–O–(3-methoxy-5-methyl)C₆H₂– | 1-ethyl-1-(N,N-dimethylamino)cyclopentyl | Free form | MS·APCI (m/z): 490 [M + H]+ |
| 1.041 | H₃C–(CH₂)₄–O–(3,5-dimethoxy)C₆H₂– | 1-ethyl-1-(N,N-dimethylamino)cyclopentyl | Free form | MS·APCI (m/z): 492 [M + H]+ |

TABLE A-continued
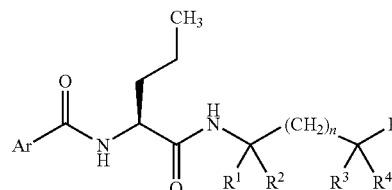
| Ex. No. | Ar | R¹ R² (CH₂)ₙ R³ R⁴ R | Salt | Physical properties, etc. |
|---|---|---|---|---|
| 1.042 | 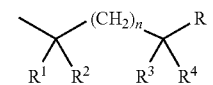 | 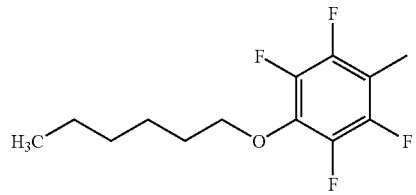 | Free form | MS·APCI (m/z): 518 [M + H]+ |
| 1.043 | 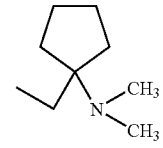 | 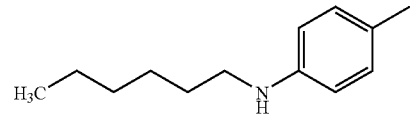 | Free form | MS·APCI (m/z): 445 [M + H]+ |
| 1.044 | 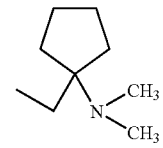 | 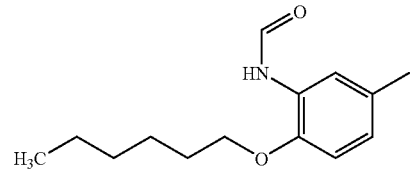 | Free form | MS·APCI (m/z): 489 [M + H]+ |
| 1.045 | 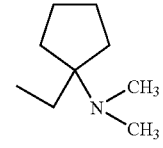 | 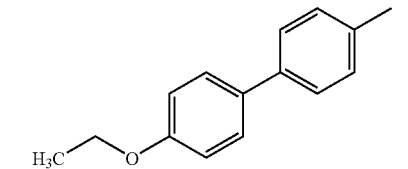 | Free form | MS·APCI (m/z): 466 [M + H]+ |
| 1.046 | 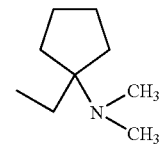 | 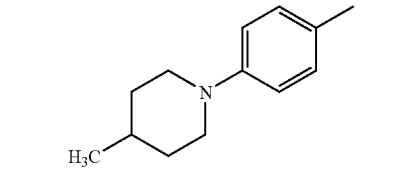 | Free form | MS·APCI (m/z): 443 [M + H]+ |
| 1.047 | 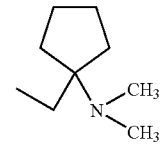 | 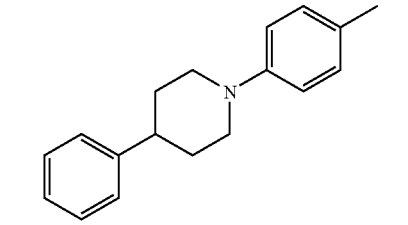 | Free form | MS·APCI (m/z): 505 [M + H]+ |

TABLE A-continued

| Ex. No. | Ar | (CH₂)ₙ R / R¹ R² R³ R⁴ | Salt | Physical properties, etc. |
|---|---|---|---|---|
| 1.048 | 6-phenyl-2-naphthyl | 1-ethyl-1-(N,N-dimethylamino)cyclopentyl | Free form | MS·APCI (m/z): 472 [M + H]+ |
| 1.049 | 6-(2-chlorophenyl)-2-naphthyl | 1-ethyl-1-(N,N-dimethylamino)cyclopentyl | Free form | MS·APCI (m/z): 508 [M + H]+ |
| 1.050 | 1-nitro-2-phenyl-6-naphthyl | 1-ethyl-1-(N,N-dimethylamino)cyclopentyl | Free form | MS·APCI (m/z): 517 [M + H]+ |
| 1.051 | 1-nitro-2-piperidino-6-naphthyl | 1-ethyl-1-(N,N-dimethylamino)cyclopentyl | Free form | MS·APCI (m/z): 524 [M + H]+ |
| 1.052 | 6-cyclohexyloxy-2-naphthyl | 1-ethyl-1-(N,N-dimethylamino)cyclopentyl | Free form | MS·APCI (m/z): 494 [M + H]+ |
| 1.053 | 3,5-dimethoxy-4-benzyloxyphenyl | 1-(N,N-dimethylamino)-1-propylcyclopentyl | Free form | MS·APCI (m/z): 526 [M + H]+ |
| 1.054 | 3,5-dimethoxy-4-benzyloxyphenyl | 1-ethyl-1-(N,N-dimethylamino)cyclohexyl | Free form | MS·APCI (m/z): 526 [M + H]+ |

TABLE A-continued
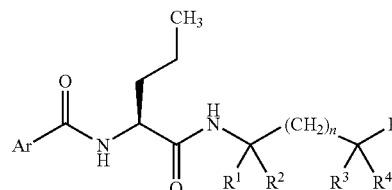
| Ex. No. | Ar | (CH₂)ₙ R¹ R² R³ R⁴ | Salt | Physical properties, etc. |
|---|---|---|---|---|
| 1.055 | 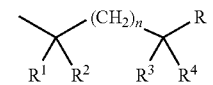 | 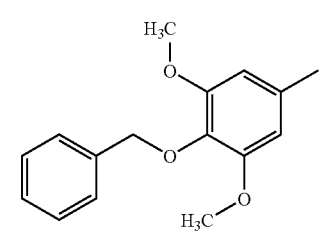 | Free form | MS · APCI (m/z): 498 [M + H]+ |
| 1.056 | 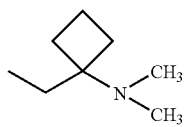 | 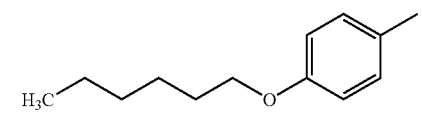 | Free form | MS · APCI (m/z): 432 [M + H]+ |
| 1.057 | 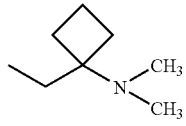 | 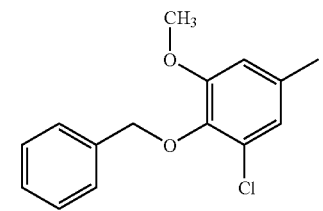 | Free form | MS · APCI (m/z): 462/464 [M + H]+ |
| 1.058 | 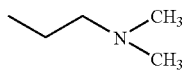 | 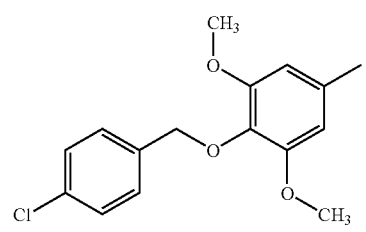 | Free form | MS · APCI (m/z): 492/494 [M + H]+ |
| 1.059 | 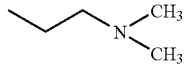 | 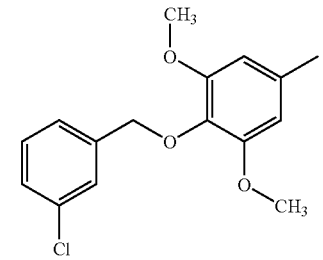 | Free form | MS · APCI (m/z): 492/494 [M + H]+ |

TABLE A-continued

[Structure: Ar-C(=O)-NH-CH(CH₂CH₂CH₃)-C(=O)-NH-C(R¹)(R²)-(CH₂)ₙ-C(R³)(R⁴)-R]

| Ex. No. | Ar | (CH₂)ₙ / R¹ R² R³ R⁴ R | Salt | Physical properties, etc. |
|---|---|---|---|---|
| 1.060 | 2,6-dimethoxy-4-methylphenyl with O-CH₂-(2-chlorophenyl) | propyl-N(CH₃)₂ | Free form | MS·APCI (m/z): 492/494 [M + H]+ |
| 1.061 | 2,6-dimethoxy-4-methylphenyl with O-CH₂-(4-fluorophenyl) | propyl-N(CH₃)₂ | Free form | MS·APCI (m/z): 476 [M + H]+ |
| 1.062 | 2,6-dimethoxy-4-methylphenyl with O-CH₂-(4-trifluoromethylphenyl) | propyl-N(CH₃)₂ | Free form | MS·APCI (m/z): 526 [M + H]+ |
| 1.063 | 2,6-dimethoxy-4-methyl-biphenyl with 4'-ethoxy | propyl-N(CH₃)₂ | Free form | MS·APCI (m/z): 472 [M + H]+ |
| 1.064 | 2,4-dimethyl-biphenyl with 4'-ethoxy | propyl-N(CH₃)₂ | Free form | MS·APCI (m/z): 426 [M + H]+ |
| 1.065 | 6-methyl-2-phenylnaphthalen-yl | propyl-N(CH₃)₂ | Free form | MS·APCI (m/z): 418 [M + H]+ |

TABLE A-continued
| Ex. No. | Ar | (CH₂)ₙ R¹ R² R³ R⁴ | Salt | Physical properties, etc. |
|---|---|---|---|---|
| 1.066 | 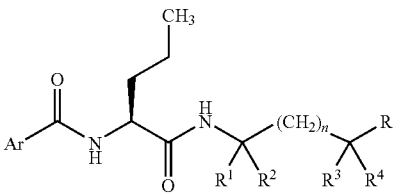 | 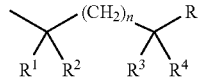 | Free form | MS · APCI (m/z): 400 [M + H]+ |
| 1.067 | 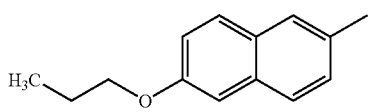 | 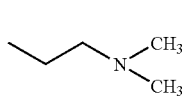 | Free form | MS · APCI (m/z): 434/436 [M + H]+ |
| 1.068 | 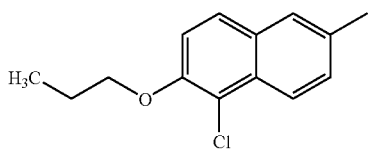 | 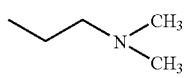 | Free form | MS · APCI (m/z): 414 [M + H]+ |
| 1.069 | 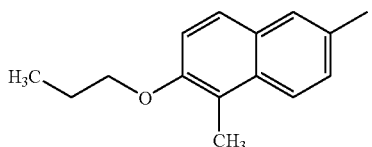 | 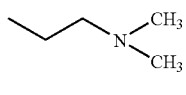 | Free form | MS · APCI (m/z): 448 [M + H]+ |
| 1.070 | 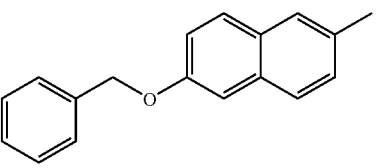 | 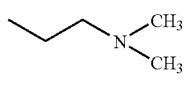 | Free form | MS · APCI (m/z): 466 [M + H]+ |
| 1.071 | 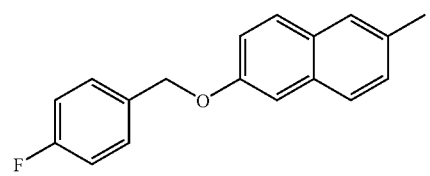 | 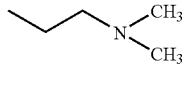 | Free form | MS · APCI (m/z): 452 [M + H]+ |
| 1.072 | 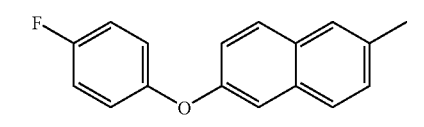 | 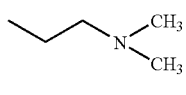 | Free form | MS · APCI (m/z): 440 [M + H]+ |
| 1.073 | 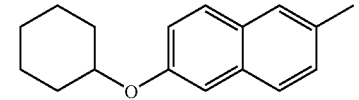 | 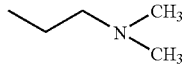 | Free form | MS · APCI (m/z): 486 [M + H]+ |

TABLE A-continued

[Structure: Ar-C(=O)-NH-CH(CH₂CH₂CH₃)-C(=O)-NH-C(R¹)(R²)-(CH₂)ₙ-C(R³)(R⁴)-R]

| Ex. No. | Ar | (CH₂)ₙ with R¹, R², R³, R⁴, R | Salt | Physical properties, etc. |
|---|---|---|---|---|
| 1.074 | 3,5-dimethoxy-4-benzyloxyphenyl | -CH₂CH₂CH₂CH₂-N(CH₃)₂ | Free form | MS·APCI (m/z): 472 [M + H]+ |
| 1.075 | 3,5-dimethoxy-4-benzyloxyphenyl | -CH₂CH₂CH₂-N(CH₂CH₃)₂ | Free form | MS·APCI (m/z): 486 [M + H]+ |
| 1.076 | 3,5-dimethoxy-4-benzyloxyphenyl | -CH₂CH₂CH₂-pyrrolidin-1-yl | Free form | MS·APCI (m/z): 484 [M + H]+ |
| 1.077 | 6-phenylnaphthalen-2-yl | -CH₂-(1-methylpiperidin-4-yl) | Free form | MS·APCI (m/z): 444 [M + H]+ |
| 1.078 | 3,5-dimethoxy-4-benzyloxyphenyl | -CH₂-(1-methylpiperidin-4-yl) | Free form | MS·APCI (m/z): 484 [M + H]+ |
| 1.079 | 3,5-dimethoxy-4-(4-chlorobenzyloxy)phenyl | -CH₂-(1-methylpiperidin-4-yl) | Free form | MS·APCI (m/z): 518/520 [M + H]+ |

TABLE A-continued

| Ex. No. | Ar | (CH₂)ₙ / R¹ R² R³ R⁴ R | Salt | Physical properties, etc. |
|---|---|---|---|---|
| 1.080 | 4-chloro-benzyl ether of 2,6-dimethoxy-4-methylphenol | $H_3C$-CH(O-propyl)-$CH_3$ | Free form | MS · APCI (m/z): 507/509 [M + H]+ |
| 1.081 | 6-phenyl-2-naphthyl | $H_3C$-CH(O-propyl)-$CH_3$ | Free form | MS · APCI (m/z): 433 [M + H]+ |
| 1.082 | 2-hydroxy-3-(hexyloxy)-5-methylphenyl | 1-ethyl-1-(N,N-dimethylamino)cyclopentyl | HCl | MS · APCI (m/z): 462 [M + H]+ |

TABLE B

| Ex. No. | Ar | (CH₂)ₙ / R¹ R² R³ R⁴ R | Salt | Physical properties, etc. |
|---|---|---|---|---|
| 2.001 | 4-(hexyloxy)-phenyl-methyl | -CH₂CH₂CH₂-N(CH₃)₂ | Free form | MS · APCI(m/z): 394 [M + H]+ |
| 2.002 | 6-phenyl-2-naphthyl | 1-ethyl-1-(N,N-dimethylamino)cyclopentyl | Free form | MS · APCI(m/z): 474 [M + H]+ |

TABLE B-continued

[Structure: Ar-C(=O)-NH-CH(CH2OCH3)-C(=O)-NH-C(R1)(R2)-(CH2)n-C(R3)(R4)-R]

| Ex. No. | Ar | (CH2)n group with R1 R2 R3 R4 R | Salt | Physical properties, etc. |
|---|---|---|---|---|
| 2.003 | 2,6-dimethoxy-3-(4-chlorobenzyloxy)-4-methylphenyl | 1-ethyl-1-(dimethylamino)cyclopentyl | Free form | MS·APCI(m/z): 548/550 [M + H]+ |
| 2.004 | 2,6-dimethoxy-3-(benzyloxy)-4-methylphenyl | 1-ethyl-1-(dimethylamino)cyclopentyl | Free form | MS·APCI(m/z): 514 [M + H]+ |
| 2.005 | 2,6-dimethoxy-3-(4-fluorobenzyloxy)-4-methylphenyl | 1-ethyl-1-(dimethylamino)cyclopentyl | HCl | MS·APCI(m/z): 532 [M + H]+ |
| 2.006 | 2,6-dimethoxy-3-(3-methylbenzyloxy)-4-methylphenyl | 1-ethyl-1-(dimethylamino)cyclopentyl | HCl | MS·APCI(m/z): 528 [M + H]+ |
| 2.007 | 2,6-dimethoxy-3-(4-methylbenzyloxy)-4-methylphenyl | 1-ethyl-1-(dimethylamino)cyclopentyl | HCl | MS·APCI(m/z): 528 [M + H]+ |

TABLE B-continued

| Ex. No. | Ar | R¹ R² (CH₂)ₙ R³ R⁴ R | Salt | Physical properties, etc. |
|---|---|---|---|---|
| 2.008 | 4-chloro-benzyloxy-3,5-dimethoxyphenyl | 1-methyl-4-piperidinyl | Free form | MS · APCI(m/z): 520/522 [M + H]+ |
| 2.009 | 4-methyl-benzyloxy-3,5-dimethoxyphenyl | 1-methyl-4-piperidinyl | Free form | MS · APCI(m/z): 500 [M + H]+ |
| 2.010 | benzyloxy-3,5-dimethoxyphenyl | 1-methyl-4-piperidinyl | Free form | MS · APCI(m/z): 486 [M + H]+ |
| 2.011 | benzyloxy-3,5-dimethoxyphenyl | 4-piperidinyl | Free form | MS · APCI(m/z): 472 [M + H]+ |

TABLE C

| Ex. No. | Ar | (CH$_2$)$_n$ R$^1$ R$^2$ R$^3$ R$^4$ R | Salt | Physical properties, etc. |
|---|---|---|---|---|
| 3.001 | H$_3$C-(CH$_2$)$_4$-O-C$_6$H$_4$-CH$_3$ | propyl-N-methylpyrrolidine | Free form | MS · APCI(m/z): 432 [M + H]+ |
| 3.002 | H$_3$C-(CH$_2$)$_4$-O-C$_6$H$_4$-CH$_3$ | propyl-morpholine | Free form | MS · APCI(m/z): 434 [M + H]+ |
| 3.003 | H$_3$C-(CH$_2$)$_4$-O-C$_6$H$_4$-CH$_3$ | propyl-N(CH$_2$CH$_2$OH)$_2$ | Free form | MS · APCI(m/z): 452 [M + H]+ |

TABLE D

| Ex. No. | Ar | (CH$_2$)$_n$ R$^1$ R$^2$ R$^3$ R$^4$ R | Salt | Physical properties, etc. |
|---|---|---|---|---|
| 4.001 | 3,5-dimethoxy-4-benzyloxyphenyl | propyl-N(CH$_3$)$_2$ | Free form | MS · APCI(m/z): 476 [M + H]+ |
| 4.002 | 3,5-dimethoxy-4-benzyloxyphenyl | 1-ethyl-1-(N,N-dimethylamino)cyclopentyl | Free form | MS · APCI(m/z): 530 [M + H]+ |

TABLE D-continued

| Ex. No. | Ar | R¹ R² (CH₂)ₙ R³ R⁴ R | Salt | Physical properties, etc. |
|---|---|---|---|---|
| 4.003 | 4-chlorobenzyloxy-3,5-dimethoxyphenyl | 1-methyl-4-methylpiperidin-4-yl | Free form | MS·APCI(m/z): 536/538 [M + H]+ |

TABLE E

| Ex. No. | Ar | R¹ R² (CH₂)ₙ R³ R⁴ R | Salt | Physical properties, etc. |
|---|---|---|---|---|
| 5.001 | 3,5-dimethoxy-4-benzyloxyphenyl | 1-ethyl-1-(dimethylamino)cyclopentyl | Free form | MS·APCI(m/z): 498 [M + H]+ |
| 5.002 | 6-phenylnaphthalen-2-yl | 1-methylpiperidin-4-yl | Free form | MS·APCI(m/z): 430 [M + H]+ |
| 5.003 | 3,5-dimethoxy-4-benzyloxyphenyl | 2-(dimethylamino)-2-methylbutan-2-yl | Free form | MS·APCI(m/z): 472 [M + H]+ |

TABLE E-continued
| Ex. No. | Ar | (CH₂)ₙ with R¹ R² R³ R⁴ R | Salt | Physical properties, etc. |
|---|---|---|---|---|
| 5.004 | 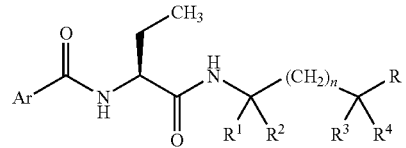 | 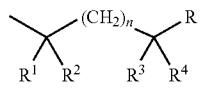 | Free form | MS · APCI(m/z): 506/508 [M + H]+ |
| 5.005 | 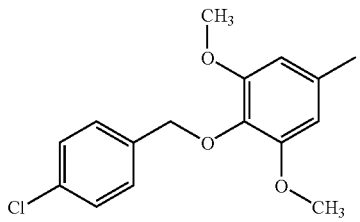 | 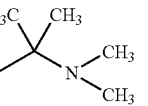 | Free form | MS · APCI(m/z): 414 [M + H]+ |
Table of Reference Examples
| Ref. Ex. No. | Structural formula | Salt | Physical properties, etc. |
|---|---|---|---|
| 1.01 |  | Free form | MS · ESI(m/z): 251 [M − H]− |
| 1.02 | 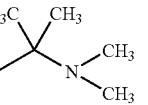 | Free form | MS · ESI(m/z): 281 [M − H]− |
| 1.03 | 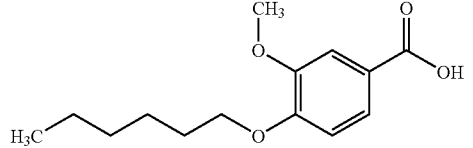 | Free form | MS · ESI(m/z): 251 [M − H]− |
| 1.04 | 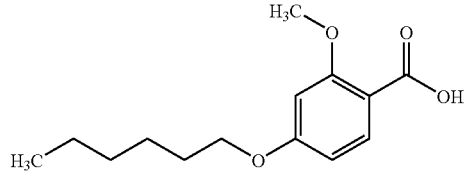 | Free form | MS · ESI(m/z): 255/257 [M − H]− |

-continued

Table of Reference Examples

| Ref. Ex. No. | Structural formula | Salt | Physical properties, etc. |
|---|---|---|---|
| 1.05 | 3,5-dichloro-4-hexyloxybenzoic acid | Free form | MS · ESI(m/z): 289/291 [M − H]− |
| 1.06 | 4-hexyloxy-3-nitrobenzoic acid | Free form | MS · ESI(m/z): 266 [M − H]− |
| 1.07 | 3-cyano-4-hexyloxybenzoic acid | Free form | MS · ESI(m/z): 246 [M − H]− |
| 1.08 | 4-hexyloxy-3,5-dimethylbenzoic acid | Free form | MS · ESI(m/z): 249 [M − H]− |
| 1.09 | 6-propoxy-2-naphthoic acid | Free form | MS · ESI(m/z): 229 [M − H]− |
| 1.10 | 3-chloro-4-hexyloxy-5-methoxybenzoic acid | Free form | MS · ESI(m/z): 285/287 [M − H]− |
| 1.11 | 4-(4-phenylbutoxy)benzoic acid | Free form | Melting point: 125-127° C. MS · EI(m/z): 270 [M]+ |
| 1.12 | 4-(pentan-2-yloxy)benzoic acid | Free form | MS · ESI(m/z): 221 [M − H]− |

-continued

Table of Reference Examples

| Ref. Ex. No. | Structural formula | Salt | Physical properties, etc. |
|---|---|---|---|
| 1.13 | 3-methoxy-4-pentyloxy-5-methoxybenzoic acid | Free form | MS·ESI(m/z): 267 [M − H]− |
| 1.14 | 3-methoxy-4-benzyloxy-5-chlorobenzoic acid | Free form | MS·ESI(m/z): 291/293 [M − H]− |
| 1.15 | 3-methoxy-4-benzyloxy-5-methoxybenzoic acid | Free form | MS·ESI(m/z): 287 [M − H]− |
| 1.16 | 3-methoxy-4-(2-chlorobenzyloxy)-5-methoxybenzoic acid | Free form | MS·ESI(m/z): 321/323 [M − H]− |
| 1.17 | 3-methoxy-4-(3-chlorobenzyloxy)-5-methoxybenzoic acid | Free form | MS·ESI(m/z): 321/323 [M − H]− |
| 1.18 | 3-methoxy-4-(4-chlorobenzyloxy)-5-methoxybenzoic acid | Free form | MS·ESI(m/z): 321/323 [M − H]− |

-continued

Table of Reference Examples

| Ref. Ex. No. | Structural formula | Salt | Physical properties, etc. |
|---|---|---|---|
| 1.19 | | Free form | MS · ESI(m/z): 355 [M − H]− |
| 1.20 | | Free form | MS · ESI(m/z): 305 [M − H]− |
| 1.21 | | Free form | MS · ESI(m/z): 301 [M − H]− |
| 1.22 | | Free form | MS · ESI(m/z): 301 [M − H]− |
| 1.23 | | Free form | MS · ESI(m/z): 263/265 [M − H]− |
| 1.24 | | Free form | MS · ESI(m/z): 277 [M − H]− |
| 1.25 | | Free form | MS · ESI(m/z): 269 [M − H]− |

-continued

Table of Reference Examples

| Ref. Ex. No. | Structural formula | Salt | Physical properties, etc. |
|---|---|---|---|
| 1.26 | 6-(4-fluorobenzyloxy)naphthalene-2-COOH | Free form | MS · ESI(m/z): 295 [M − H]− |
| 1.27 | 4-(hexyloxy)-2,3,5,6-tetrafluoro... COOH | Free form | MS · ESI(m/z): 293 [M − H]− |
| 1.28 | 4-(hexylamino)benzoic acid | Free form | MS · ESI(m/z): 220 [M − H]− |
| 1.29 | 4-(4-phenylpiperidin-1-yl)benzoic acid | Free form | MS · ESI(m/z): 280 [M − H]− |
| 1.30 | 4-(4-methylpiperidin-1-yl)benzoic acid | Free form | MS · ESI(m/z): 218 [M − H]− |
| 1.31 | 3-(methoxymethoxy)-4-(hexyloxy)benzoic acid | Free form | MS · ESI(m/z): 281 [M − H]− |
| 1.32 | 3-methoxy-4-(hexyloxy)-5-methylbenzoic acid | Free form | MS · ESI(m/z): 265 [M − H]− |
| 1.33 | 6-ethoxy-5-methylnaphthalene-2-COOH | Free form | MS · ESI(m/z): 243 [M − H]− |
| 1.34 | 3-formamido-4-(hexyloxy)benzoic acid | Free form | MS · ESI(m/z): 264 [M − H]− |

-continued

Table of Reference Examples

| Ref. Ex. No. | Structural formula | Salt | Physical properties, etc. |
|---|---|---|---|
| 1.35 | 6-phenyl-naphthalene-2-COOH | Free form | MS·ESI(m/z): 247 [M − H]− |
| 1.36 | 6-(2-chlorophenyl)-naphthalene-2-COOH | Free form | MS·ESI(m/z): 281/283 [M − H]− |
| 1.37 | 3,5-dimethoxy-4-(4-ethoxybenzyloxy)benzoic acid | Free form | MS·ESI(m/z): 301 [M − H]− |
| 1.38 | 4'-ethoxy-2-methyl-biphenyl-4-COOH | Free form | MS·ESI(m/z): 255 [M − H]− |
| 1.39 | 1-nitro-2-phenyl-naphthalene-6-COOH | Free form | MS·ESI(m/z): 292 [M − H]− |
| 1.40 | 1-nitro-2-piperidino-naphthalene-6-COOH | Free form | MS·ESI(m/z): 299 [M − H]− |
| 1.41 | 6-(4-fluorophenoxy)-naphthalene-2-COOH | Free form | MS·ESI(m/z): 281 [M − H]− |
| 2.01 | $H_2N-CH_2-C(CH_3)_2-N(CH_3)_2$ | 2HCl | MS·APCI(m/z): 117 [M + H]+ |
| 2.02 | 1-(aminomethyl)-1-(dimethylamino)cyclobutane | 2HCl | MS·APCI(m/z): 129 [M + H]+ |

-continued

Table of Reference Examples

| Ref. Ex. No. | Structural formula | Salt | Physical properties, etc. |
|---|---|---|---|
| 2.03 | | 2HCl | Melting point: 225-227° C. (decomposed) MS · APCI(m/z): 143 [M + H]+ |
| 2.04 | | 2HCl | MS · APCI(m/z): 157 [M + H]+ |
| 2.05 | | 2HCl | MS · APCI(m/z): 157 [M + H]+ |

The invention claimed is:

1. A norvaline derivative of the formula [I]:

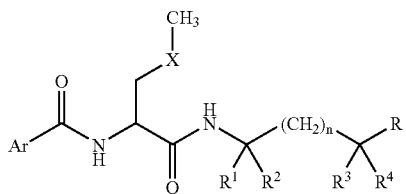

wherein

X is —CH$_2$—, —O—, —S— or a single bond;

Ar is a substituted or unsubstituted phenyl, a substituted or unsubstituted naphthyl, or a substituted or unsubstituted lower cycloalkyl;

n is an integer of 0 to 2;

$R^1$ and $R^2$ are the following (i), (ii) or (iii):
 (i) each is independently a hydrogen atom or a lower alkyl;
 (ii) $R^1$ and $R^2$ are combined together to form a lower alkylene; or
 (iii) $R^1$ is a hydrogen atom or a lower alkyl and $R^2$ is combined together with $R^4$ or $R^6$ to form a lower alkylene, when R is

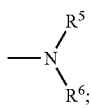

$R^3$ and $R^4$ are the following (i), (ii) or (iii):
 (i) each is independently a hydrogen atom or a lower alkyl;
 (ii) $R^3$ and $R^4$ are combined together to form a lower alkylene; or
 (iii) $R^3$ is a hydrogen atom or a lower alkyl and $R^4$ is combined together with $R^2$ or $R^6$ to form a lower alkylene, when R is

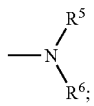

R is

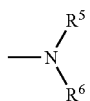

or —OR$^7$;

wherein $R^5$ and $R^6$ are the following (i), (ii) or (iii):
 (i) each is independently an unsubstituted lower alkyl or a lower alkyl substituted with hydroxyl group(s), or a hydrogen atom;
 (ii) $R^5$ and $R^6$ are combined together with the adjacent nitrogen atom to form an unsubstituted or substituted nitrogen-containing aliphatic 5- to 6-membered heterocyclic group;
 (iii) $R^5$ is an unsubstituted lower alkyl or a lower alkyl substituted with hydroxyl group(s), or a hydrogen atom, and $R^6$ is combined together with $R^2$ or $R^4$ to form a lower alkylene;

$R^7$ is a lower alkyl;

provided that when $R^5$ and $R^6$ are combined together with the adjacent nitrogen atom to form a morpholine ring, then Ar has at least one substituent other than halogen atom, methoxy or phenyl;

in free form, or a pharmaceutically acceptable salt thereof.

2. The compound according to claim 1, which is the formula [Ia]:

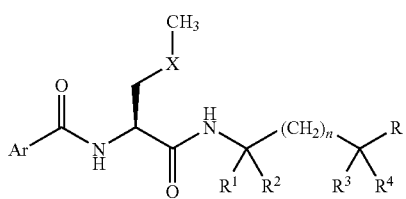

wherein, the symbols are as defined above.

3. The compound according to claim 1, wherein X is —CH$_2$—.

4. The compound according to claim 1, wherein X is —O—.

5. The compound according to claim 1, wherein X is —S—.

6. The compound according to claim 1, wherein X is a single bond.

7. The compound according to claim 1, wherein the substituent(s) of the substituted phenyl, the substituted naphthyl, or the substituted lower cycloalkyl represented by Ar is group(s) selected from the group consisting of:
halogen atom; nitro group; cyano group; hydroxyl group; an unsubstituted amino group or an amino group substituted with at least one of lower alkyl or formyl; C$_1$-7 alkyl; an unsubstituted or substituted lower alkoxy; wherein the substituted of said lower alkoxy is an unsubstituted or substituted phenyl group, and wherein the substituents of said substituted phenyl group are selected from halogen atom, lower alkyl or halo(lower)alkyl; lower cycloalkoxy; lower alkylthio; an unsubstituted or substituted phenyl, wherein the substituents on the substituted phenyl are selected from halogen atom, lower alkyl or lower alkoxy; an unsubstituted or substituted 1-piperidyl, wherein the substituents on the substituted 1-piperidyl are selected from lower alkyl or phenyl; an unsubstituted or substituted phenoxy, wherein the substituents on the substituted phenoxy are halogen atom(s).

8. The compound according to any one of claim 1 to 6 or 7 wherein Ar is a group selected from an unsubstituted or substituted phenyl and an unsubstituted or substituted naphthyl.

9. The compound according to claim 8, wherein R is

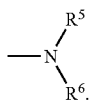

10. The compound according to claims 9, wherein a nitrogen-containing aliphatic 5- to 6-membered heterocyclic group portion of the unsubstituted or substituted nitrogen-containing aliphatic 5- to 6-membered heterocyclic group formed by $R^5$ and $R^6$ together with the adjacent nitrogen is 1-pyrrolidinyl, 1-piperidyl or 1-piperazinyl.

11. The compound according to claim 7, wherein the substituent(s) on the substituted nitrogen-containing aliphatic 5- or 6-membered heterocyclic group formed by $R^5$ and $R^6$ together with the adjacent nitrogen is lower alkyl.

12. A method for inhibiting GlyT2, which comprises: administering to a patient a therapeutically effective dose of a compound of the formula [I]:

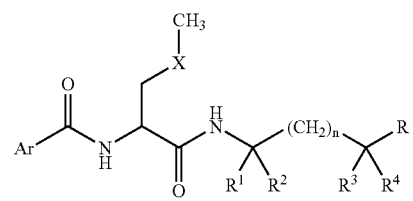

wherein
X is —CH$_2$—, —O—, —S— or a single bond;
Ar is a substituted aryl, an unsubstituted aryl, a substituted lower cycloalkyl or unsubstituted lower cycloalkyl;
n is an integer of 0 to 2;
$R^1$ and $R^2$ are the following (i), (ii) or (iii):
  (i) each is independently a hydrogen atom or a lower alkyl;
  (ii) $R^1$ and $R^2$ are combined together to form a lower alkylene; or
  (iii) $R^1$ is a hydrogen atom or a lower alkyl and $R^2$ is combined together with $R^4$ or $R^6$ to form a lower alkylene, when R is

$R^3$ $R^4$ are the following (i), (ii) or (iii):
  (i) each is independently a hydrogen atom or a lower alkyl;
  (ii) $R^3$ and $R^4$ are combined together to form a lower alkylene; or
  (iii) $R^3$ is a hydrogen atom or a lower alkyl and $R^4$ is combined together with $R^2$ or $R^6$ to form a lower alkylene, when R is

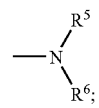

R is

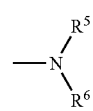

or —OR$^7$;
wherein $R^5$ and $R^6$ are the following (i), (ii) or (iii):
  (i) each is independently an unsubstituted lower alkyl or a lower alkyl substituted with hydroxyl group(s), or a hydrogen atom;
  (ii) $R^5$ and $R^6$ are combined together with the adjacent nitrogen atom to form an unsubstituted or substituted nitrogen-containing aliphatic 5- to 6-membered heterocyclic group;

(iii) $R^5$ is an unsubstituted lower alkyl or a lower alkyl substituted with hydroxyl group(s), or a hydrogen atom, and $R^6$ is combined together with $R^2$ or $R^4$ to form a lower alkylene;

$R^7$ is a lower alkyl;

provided that when $R^5$ and $R^6$ are combined together with the adjacent nitrogen atom to form a morpholine ring, then Ar has at least one substituent other than halogen atom, methoxy or phenyl;

and when R is —$OR^7$ and X is a single bond, then Ar is a substituted or unsubstituted phenyl, a substituted or unsubstituted naphthyl or a substituted or unsubstituted lower cycloalkyl, in free form, or a pharmaceutically acceptable salt thereof.

13. A pharmaceutical composition comprising the compound according to claim 1 as an effective ingredient and a pharmaceutically acceptable carrier selected from the group consisting of binder, excipients, lubricants, disintegrators, distilled water, physiological saline, and an aqueous glucose solution.

* * * * *

UNITED STATES PATENT AND TRADEMARK OFFICE
CERTIFICATE OF CORRECTION

PATENT NO. : 7,718,703 B2
APPLICATION NO. : 11/795966
DATED : May 18, 2010
INVENTOR(S) : Naoyuki Harada et al.

It is certified that error appears in the above-identified patent and that said Letters Patent is hereby corrected as shown below:

ON THE TITLE PAGE:

Insert the following as item (60), Related U.S. Application Data:

--Provisional application No. 60/646,502, filed on Jan. 25, 2005--.

Correct item (86) as follows:

"PCT/JP2006/001394" should read --PCT/JP2006/301394--.

IN THE CLAIMS:

Claim 7, line 7 (at column 71, line 31), "$C_1$-7" should read --$C_{1-7}$--.

Claim 12, line 19 (at column 72, line 35), "$R^3$ $R^4$" should read --$R^3$ and $R^4$--.

Signed and Sealed this
Eighth Day of March, 2011

David J. Kappos
*Director of the United States Patent and Trademark Office*